(12) United States Patent
Stayton et al.

(10) Patent No.: US 8,507,283 B2
(45) Date of Patent: Aug. 13, 2013

(54) STIMULI-RESPONSIVE MAGNETIC NANOPARTICLES AND RELATED METHODS

(75) Inventors: Patrick S. Stayton, Seattle, WA (US); Allan S. Hoffman, Seattle, WA (US); Jr-iuan Lai, Seattle, WA (US); John Hoffman, Seattle, WA (US); Mitsuhiro Ebara, Mino (JP)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 13/161,233

(22) Filed: Jun. 15, 2011

(65) Prior Publication Data

US 2011/0266492 A1 Nov. 3, 2011

Related U.S. Application Data

(63) Continuation of application No. 11/683,889, filed on Mar. 8, 2007, now Pat. No. 7,981,688.

(51) Int. Cl.
*G01N 33/20* (2006.01)

(52) U.S. Cl.
USPC .............................. 436/73; 436/75; 436/149

(58) Field of Classification Search
None
See application file for complete search history.

(56) References Cited

U.S. PATENT DOCUMENTS

| | | | |
|---|---|---|---|
| 4,332,690 A | 6/1982 | Kimura |
| 4,657,543 A | 4/1987 | Langer |
| 4,780,409 A | 10/1988 | Monji |
| 5,135,876 A | 8/1992 | Andrade |
| 5,356,713 A | 10/1994 | Charmot |
| 5,362,308 A | 11/1994 | Chien |
| 5,378,608 A | 1/1995 | Marui |
| 5,451,411 A | 9/1995 | Gombotz |
| 5,466,348 A | 11/1995 | Holm-Kennedy |
| 5,501,584 A | 3/1996 | Yamamoto |
| 5,521,291 A | 5/1996 | Curiel |
| 5,547,932 A | 8/1996 | Curiel |
| 5,569,364 A | 10/1996 | Hooper |
| 5,599,908 A | 2/1997 | Raso |
| 5,603,931 A | 2/1997 | Raso |
| 5,609,590 A | 3/1997 | Herbig |
| 5,656,609 A | 8/1997 | Wu |
| 5,753,263 A | 5/1998 | Lishko |
| 5,770,627 A | 6/1998 | Inoue |
| 5,807,306 A | 9/1998 | Shapland |
| 5,827,743 A | 10/1998 | Tanzawa |

(Continued)

FOREIGN PATENT DOCUMENTS

| | | |
|---|---|---|
| DE | 697 06 501 T2 | 5/2002 |
| DE | 102 24 352 A1 | 12/2003 |

(Continued)

OTHER PUBLICATIONS

Lai et al. "Dual Magnetic-/Temperature-Responsive Nanoparticles for Microfluidic Separations and Assays". 2007. Langmuir. vol. 23, pp. 7385-7391.*

(Continued)

*Primary Examiner* — Yelena G Gakh
(74) *Attorney, Agent, or Firm* — Christensen O'Connor Johnson Kindness PLLC

(57) ABSTRACT

Stimuli-responsive magnetic nanoparticles, methods of making the nanoparticles, and methods of using the nanoparticles.

20 Claims, 8 Drawing Sheets

(56) References Cited

U.S. PATENT DOCUMENTS

| | | |
|---|---|---|
| 5,876,989 A | 3/1999 | Berg |
| 5,939,453 A | 8/1999 | Heller |
| 5,997,961 A | 12/1999 | Feng |
| 5,998,588 A | 12/1999 | Hoffman |
| 6,133,047 A | 10/2000 | Elaissari |
| 6,165,509 A | 12/2000 | Hoffman |
| 6,210,717 B1 | 4/2001 | Choi |
| 6,355,163 B2 | 3/2002 | Hindsgaul |
| 6,426,086 B1 | 7/2002 | Papahadjopoulos |
| 6,447,764 B1 | 9/2002 | Bayer |
| 6,486,213 B1 | 11/2002 | Chen |
| 6,521,341 B1 | 2/2003 | Elaissari |
| 6,641,735 B1 | 11/2003 | Yoshizako |
| 6,740,409 B1 | 5/2004 | Granick |
| 6,835,393 B2 | 12/2004 | Hoffman |
| 7,060,804 B2 | 6/2006 | Elaissari |
| 7,195,925 B2 | 3/2007 | Ohnishi |
| 7,393,698 B2 | 7/2008 | Furukawa |
| 7,625,764 B2 | 12/2009 | Stayton |
| 7,695,905 B2 | 4/2010 | Furukawa |
| 7,718,193 B2 | 5/2010 | Stayton |
| 7,732,550 B2 | 6/2010 | Ohnishi |
| 7,976,728 B2 | 7/2011 | Eguchi |
| 7,981,688 B2 | 7/2011 | Stayton |
| 8,105,493 B2 | 1/2012 | Takahashi |
| 2001/0027072 A1 | 10/2001 | Mumick |
| 2003/0165962 A1 | 9/2003 | Furukawa |
| 2003/0175691 A1 | 9/2003 | Elaissari |
| 2003/0175826 A1 | 9/2003 | Furukawa |
| 2003/0218130 A1 | 11/2003 | Boschetti |
| 2004/0077024 A1 | 4/2004 | Holmberg |
| 2004/0239738 A1 | 12/2004 | Watanabe |
| 2005/0124728 A1 | 6/2005 | Komatsu |
| 2005/0130167 A1* | 6/2005 | Bao et al. .................. 435/6 |
| 2005/0137334 A1 | 6/2005 | Mondain-Monval |
| 2005/0158782 A1 | 7/2005 | Furukawa |
| 2005/0175702 A1 | 8/2005 | Müller-Schulte |
| 2007/0218567 A1 | 9/2007 | Tanaka |
| 2008/0199884 A1 | 8/2008 | Ohnishi |
| 2008/0220531 A1 | 9/2008 | Stayton |
| 2008/0293118 A1 | 11/2008 | Furukawa |
| 2009/0001025 A1 | 1/2009 | Takahashi |
| 2009/0001321 A1 | 1/2009 | Eguchi |
| 2010/0062433 A1 | 3/2010 | Nagaoka |
| 2010/0168044 A1 | 7/2010 | Misra |
| 2010/0215749 A1 | 8/2010 | Stayton |
| 2010/0330688 A1 | 12/2010 | Sawai |
| 2011/0003392 A1 | 1/2011 | Stayton |
| 2011/0014713 A1 | 1/2011 | Sawai |
| 2011/0097416 A1 | 4/2011 | Nguyen |
| 2011/0117668 A1 | 5/2011 | Stayton |
| 2011/0120919 A1 | 5/2011 | Domke |
| 2011/0155947 A1 | 6/2011 | Eguchi |
| 2011/0233453 A1 | 9/2011 | Eguchi |

FOREIGN PATENT DOCUMENTS

| | | |
|---|---|---|
| DE | 698 39 323 T2 | 4/2009 |
| EP | 0 693 508 A1 | 8/1995 |
| EP | 1 281 436 A1 | 8/1995 |
| EP | 1 312 671 A1 | 5/2003 |
| EP | 1 316 599 A1 | 6/2003 |
| EP | 1 396 508 A1 | 10/2004 |
| EP | 1 803 467 A1 | 7/2007 |
| EP | 2 009 044 A1 | 12/2008 |
| EP | 2 009 442 A2 | 12/2008 |
| EP | 2 037 272 A1 | 3/2009 |
| EP | 1 509 246 B1 | 5/2009 |
| EP | 2 237 036 A1 | 10/2010 |
| EP | 2 246 701 A1 | 11/2010 |
| EP | 2 313 200 A1 | 4/2011 |
| EP | 2 320 437 A1 | 5/2011 |
| GB | 2 439 846 B | 10/2009 |
| GB | 2 435 647 B | 3/2010 |
| GB | 2 431 472 B | 4/2011 |
| JP | 2002-223793 A | 8/2002 |
| JP | 2004-201648 A | 7/2004 |
| JP | 2005-060244 A | 3/2005 |
| JP | 2005-082538 A | 3/2005 |
| JP | 2005-537342 A | 12/2005 |
| JP | 2006-194635 A | 7/2006 |
| JP | 2006-208368 A | 8/2006 |
| JP | 2006-242597 A | 9/2006 |
| JP | 2006-327962 A | 12/2006 |
| JP | 2007-056094 A | 3/2007 |
| JP | 2007-248349 A | 9/2007 |
| JP | 2007-256024 A | 10/2007 |
| JP | 2007-262388 A | 10/2007 |
| JP | 2008-232716 A | 10/2008 |
| JP | 2009-013207 A | 1/2009 |
| JP | 2009-028711 A | 2/2009 |
| JP | 2009-162532 A | 7/2009 |
| JP | 2009-162534 A | 7/2009 |
| JP | 2009-171853 A | 8/2009 |
| JP | 2009-189306 A | 8/2009 |
| JP | 2009-281728 A | 12/2009 |
| JP | 2010-032360 A | 2/2010 |
| JP | 2010-062444 A | 3/2010 |
| JP | 2010-066200 A | 3/2010 |
| JP | 2010-151528 A | 7/2010 |
| JP | 2010-235441 A | 10/2010 |
| WO | 00/43355 A1 | 7/2000 |
| WO | 01/51092 A2 | 7/2001 |
| WO | 02/16528 A1 | 2/2002 |
| WO | 02/16571 A1 | 2/2002 |
| WO | 03/055590 A2 | 7/2003 |
| WO | 2005/021612 A1 | 3/2005 |
| WO | 2006/022340 A1 | 3/2006 |
| WO | 2008/111687 A1 | 9/2008 |
| WO | 2009/084595 A1 | 7/2009 |
| WO | 2009/126441 A1 | 10/2009 |
| WO | 2009/140421 A2 | 11/2009 |
| WO | 2009/140429 A2 | 11/2009 |
| WO | 2009/140432 A1 | 11/2009 |
| WO | 2010/007157 A1 | 1/2010 |
| WO | 2010/021770 A1 | 2/2010 |
| WO | 2010/053597 A1 | 5/2010 |

OTHER PUBLICATIONS

Matsuno et al. "Polystyrene- and Poly(3-vinylpyridine)-Grafted Magnetite Nanoparticles Prepared through Surface-Initiated Nitroxide-Mediated Radical Polymerization", Macromolecules, 2004, v. 37, pp. 2203-2209.*

Garcia et al. "Generation of Core/Shell Iron Oxide Magnetic Nanoparticles with Polystyrene Brushes by Atom Transfer Radical Polymerization", Journal of Polymer Science: Part A: Polymer Chemistry, 2007, vol. 45, pp. 4744-4750.*

Wu et al. "Magnetic Iron Oxide Nanoparticles: Synthesis and Surface Functionalization Strategies", Nanoscale Res. Lett., 2008, v. 3, pp. 397-415.*

Zhang et al. "Preparation and characterization of thermosensitive PNIPAA-coated iron oxide nanoparticles", Nanotechnology, 2008, v. 19, 325608 (4pp).*

Medeiros et al. "Stimuli-responsive magnetic particles for biomedical applications", International Journal of Pharmaceutics 2011, v. 403, pp. 139-161.*

Thorek et al. "Superparamagnetic Iron Oxide Nanoparticle Probes for Molecular Imaging", Annals of Biomedical Engineering, Jan. 2006, vol. 34, No. 1, pp. 23-38.*

Uhlmann et al. "Surface functionalization by smart coatings: Stimuli-responsive binary polymer brushes", Progress in Organic Coatings, 2006, v. 55, pp. 168-174.*

Abu-Lail et al. "Micro-cantilevers with end-grafted stimulus-responsive polymer brushes for actuation and sensing", Sensors and Actuators B, 2006, v. 114, pp. 371-378.*

Irie, M., "Stimuli-Response Poly(N-isopropylacrylamide). Photo- and Chemical-Induced Phase Transitions," Advances in Polymer Science 110:49-65, 1993.

Guo, J., et al., "Poly(N-isopropylacrylamide)-Coated Luminescent/Magnetic Silica Microspheres: Preparation, Characterization, and Biomedical Applications," Chemistry of Materials 18(23):5554-5562, Nov. 2006.

Li, M, et. al., "Organization of Inorganic Nanoparticles Using Biotin-Streptavidin Connectors," Chemistry of Materials 11(1):Jan. 23-26, 1999.

Akiyoshi, K., et al., "Controlled Association of Amphiphilic Polymers in Water: Thermosensitive Nanoparticles Formed by Self-Assembly of Hydrophobically Modified Pullulans and Poly(N-isopropylacrylamides)," Macromolecules 33(9):3244-3249, May 2000.

Buchholz, B.A., et al., "Microchannel DNA Sequencing Matrices With Switchable Viscosities," Electrophoresis 23(10):1398-1409, May 2002.

Frey, N.A., et al., "Magnetic Nanoparticles: Synthesis, Functionalization, and Applications in Bioimaging and Magnetic Energy Storage," Chemical Society Reviews 38(9):2532-2542, Sep. 2009.

Golden, A.L., et al., "Simple Fluidic System for Purifying and Concentrating Diagnostic Biomarkers Using Stimuli-Responsive Antibody Conjugates and Membranes," Bioconjugate Chemistry 21(10):1820-1826, Oct. 2010.

Hoffman, J.M., et al., "A Helical Flow, Circular Microreactor for Separating and Enriching 'Smart' Polymer—Antibody Capture Reagents," Lab on a Chip 10(22):3130-3138, Nov. 2010.

Hoffman, A.S., et al., "Really Smart Bioconjugates of Smart Polymers and Receptor Proteins," Journal of Biomedical Materials Research 52(4):577-586, Dec. 2000.

International Search Report and Written Opinion mailed Sep. 15, 2011, issued in corresponding International Application No. PCT/US2011/035256, filed May 4, 2011, 12 pages.

International Search Report and Written Opinion mailed Feb. 22, 2012, issued in corresponding International Application No. PCT/US2011/040385, filed Jun. 14, 2011, 10 pages.

Kanazawa, H., and Y. Matsushima, "Temperature-Responsive Chromatography," Trends in Analytical Chemistry 17(7):435-440, Aug. 1998.

Kondo, A., and H. Fukuda, "Preparation of Thermo-Sensitive Magnetic Hydrogel Microspheres and Application to Enzyme Immobilization," Journal of Fermentation and Bioengineering 84(4):337-341, Jan. 1997.

Kondo, A., et al., "Development and Application of Thermo-Sensitive Magnetic Immunomicrospheres for Antibody Purification," Applied Microbiology and Biotechnology 41(1):99-105, Mar. 1994.

Kulkarni, S., et al., "Reversible Meso-Scale Smart Polymer—Protein Particles of Controlled Sizes," Bioconjugate Chemistry 15(4):747-753, Jul. 2004.

Malmstadt, N., et al., "A Smart Microfluidic Affinity Chromatography Matrix Composed of Poly(N-isopropylacrylamide)-Coated Beads," Analytical Chemistry 75(13):2943-949, Jul. 2003.

Malmstadt, N., et al., "'Smart' Mobile Affinity Matrix for Microfluidic Immunoassays," Lab on a Chip 4(4):412-415, Aug. 2004.

Matsubara, C., et al., "Determination of Trace Amounts of Phosphate in Water After Preconcentration Using a Thermally Reversible Polymer," Analyst 118(5):553-556, May 1993.

Miura, M., et al., "Application of LCST Polymer-Cell Receptor Conjugates for Cell Culture on Hydrophobic Surfaces," 17th Annual Meeting of the Society for Biomaterials, Scottsdale, Ariz., May 1-5, 1991, p. 130.

Monji, N., and A.S. Hoffman, "A Novel Immunoassay System and Bioseparation Process Based on Thermal Phase Separating Polymers," Applied Biochemistry and Biotechnology 14(2):107-120, Mar. 1987.

Monji, N., et al., "Application of a Thermally-Reversible Polymer—Antibody Conjugate in a Novel Membrane-Based Immunoassay," Biochemical and Biophysical Research Communications 172(2):652-660, Oct. 1990.

Nash, M.A., et al., "Mixed Stimuli-Responsive Magnetic and Gold Nanoparticle System for Rapid Purification, Enrichment, and Detection of Biomarkers," Bioconjugate Chemistry 21(12):2197-2204, Dec. 2010.

Nash, M.A., et al., "'Smart' Diblock Copolymers as Templates for Magnetic-Core Gold-Shell Nanoparticle Synthesis," Nano Letters 10(1):85-91, Jan. 2010.

Tang, Z., et al., "Single Nucleotide Polymorphisms (SNPs) Assay Using Reversible Association and Dispersion of DNA-Linked Colloidal Nanoparticles," Nucleic Acids Research: Supplement No. 1, Nov. 2001, pp. 165-166.

Yoshizako, K., and Y. Akiyama, "Regulation of Protein Binding Toward a Ligand on Chromatographic Matrixes by Masking and Forced-Releasing Effects Using Thermoresponsive Polymer," Analytical Chemistry 74(16):4160-4166, Aug. 2002.

* cited by examiner

STIMULI-RESPONSIVE MAGNETIC NANOPARTICLES AND RELATED METHODS

CROSS-REFERENCE TO RELATED APPLICATION

This application is a continuation of U.S. application Ser. No. 11/683,889, filed Mar. 8, 2007, which is incorporated herein by reference in its entirety.

STATEMENT OF GOVERNMENT LICENSE RIGHTS

This invention was made with Government support under contract number 5 R01 EB 00252-09 awarded by the National Institutes of Health, National Institute of Biomedical Imaging and Bioengineering. The Government has certain rights in the invention.

BACKGROUND

The present invention relates to stimuli-responsive magnetic nanoparticles, methods for making the nanoparticles, and methods for using the nanoparticles.

There has been considerable recent interest in the development of magnetic nanoparticle (mNP) technologies for diagnostic and imaging applications. Compared to larger magnetic particles, the smaller nanoparticles (NPs) display potential advantages in their diffusive and superparamagnetic properties. Magnetophoretic mobility, $\mu_m$, is defined as the acceleration of an object in the presence of a magnetic field, which determines the ability to control the object's movement within a magnetic field. The for an individual particle at room temperature and above is defined as $$\mu_m = \frac{\pi \mu_0 M_{S,C}^2 D_C^5}{324 k_B T \eta}$$

where $\mu_0$ is the magnetic constant, $M_{S,C}$ is the saturation magnetic moment of the mNPs, $D_C$ is the diameter of the mNPs, $k_B$ is the Boltzmann constant, $\eta$ is the viscosity of the medium, and T is the temperature. Because of their small particle size, which results in randomized magnetic moments, the $\mu_m$ for mNPs is usually small. This leads to an intrinsic challenge for applications where the favorable diffusive properties of the small mNPs are advantageous, for example, where the mNPs are used to capture diagnostic targets via antibody-antigen interactions. On the one hand, the small particles display better association and binding properties, but on the other hand their small size reduces magnetic capture efficiency.

Approaches to overcoming the small $\mu_m$ for mNPs include using larger macromolecules or objects that are labeled with multiple mNPs, making the mNPs from materials with larger $M_{S,C}$, using irreversibly aggregated mNPs, or using high magnetic gradients. However, most of these approaches result in the loss of favorable diffusive properties and suffer some drawbacks in the microfluidic-based diagnostic device environment. High magnetic gradients require a large number of coils and high current, which cannot be easily integrated into microfluidic devices. Materials with high $M_{S,C}$ are usually metals or alloys and, because of their high surface/volume ratio, they are prone to oxidation events that can lower their $M_{S,C}$. The pre-aggregation of mNPs into larger structures results in the permanent lowering of surface/volume ratio and to a decrease in the mNPs favorable diffusive properties.

There is a need for mNPs with favorable diffusive properties that can also be readily separated in a small magnetic field.

Stimuli-responsive ("intelligent" or "smart") materials and molecules exhibit abrupt property changes in response to small changes in external stimuli such as pH; temperature; UV-visible light; ionic strength; the concentration of certain chemicals, such as polyvalent ions, polyions of either charge, or enzyme substrates, such as glucose; as well as upon photo-irradiation or exposure to an electric field. Normally these changes are fully reversible once the stimulus has been removed.

Poly(N-isopropylacrylamide) (PNIPAAm) is a temperature-responsive polymer that exhibits a lower critical solution temperature (LCST) around which the polymer reversibly aggregates. Below the LCST, PNIPAAm chains hydrate to form an expanded structure; above the LCST, PNIPAAm chains dehydrate to form a shrinkage structure. This property is due to the thermally-reversible interaction of water molecules with the hydrophobic groups, especially the isopropyl groups, leading to low entropy, hydrophobically-bound water molecules below the LCST and release of those water molecules at and above the LCST. Modification of mNPs with PNIPAAm yields particles that can be reversibly aggregated in solution as the temperature is cycled through the LCST.

Previous work with PNIPAAm-modified mNPs has relied on post-synthesis chemical modification of the particles. Chiu et al. synthesized a $Fe_3O_4$ ferrofluid by co-precipitating $FeCl_3$ and $FeCl_2$. The ferrofluid was then mixed with a PNIPAAm solution and crosslinked to form magnetic polymeric networks. Lin, C. L. and W. Y. Chiu, *J. Polym. Sci., Part A: Polym. Chem.* 2005, 43, 5923-5934. Wang et al. also co-precipitated $FeCl_3$ and $FeCl_2$ to synthesize $Fe_3O_4$ particles. Deng, Y., et al., *Adv. Mater.* 2003, 15, 1729-1732. The particles were coated with a layer of silica and modified with 3-aminopropyltrimethoxysilane to seed the precipitation polymerization of NIPAAm. In both methods, the post-synthesis functionalization requires multiple steps and can result in particle aggregation. There is a need for methods of making stimuli-responsive polymer-modified mNPs that do not require extensive post-synthesis workup steps and result in minimal particle aggregation.

Stimuli-responsive materials and molecules have numerous possible applications in the biomedical/pharmaceutical field, as well as in biotechnology and the related industries. Smart conjugates, smart surfaces, smart polymeric micelles, and smart hydrogels have all been studied for a variety of diagnostics, separations, cell culture, drug delivery, and bioprocess applications.

Despite the development of magnetic nanoparticle (mNP) technologies for diagnostic and imaging applications, there exists a need for a stimuli-responsive magnetic nanoparticle with favorable diffusive properties as well as with the ability to be reversibly aggregated into larger structures, and simpler methods for making the nanoparticles. The present invention seeks to fulfill these needs and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the invention provides a stimuli-responsive magnetic nanoparticle having responsivity to a magnetic field, comprising:
(a) a core having responsivity to a magnetic field; and
(b) a plurality of stimuli-responsive polymers attached to the core, wherein the polymer terminates with a functional group capable of covalent coupling with a capture molecule.

In another aspect, the invention provides a stimuli-responsive magnetic nanoparticle, comprising:
(a) a core having responsivity to a magnetic field; and
(b) a plurality of stimuli-responsive polymers attached to the core, wherein the polymer terminates with a capture moiety.

In another aspect, the invention provides a method for making stimuli-responsive nanoparticles.

In one embodiment, the stimuli-responsive nanoparticles are made by
(a) providing a plurality of stimuli-responsive polymers to form a micelle having a hydrophobic core; and
(b) loading the hydrophobic core with material having responsivity to a magnetic field.

In one embodiment, the stimuli-responsive nanoparticle are made by
(a) providing a plurality of stimuli-responsive polymers to form a micelle having a hydrophobic core; and
(b) using the hydrophobic core as dimensional confinement to synthesize a core having responsivity to a magnetic field.

In other aspects, the invention provides methods for using the nanoparticle.

In one embodiment, the invention provides a method for capturing a diagnostic target, comprising:
(a) contacting a medium comprising a diagnostic target with a plurality of stimuli-responsive magnetic nanoparticles, wherein each nanoparticle comprises a capture moiety reactive toward the diagnostic target;
(b) applying an external stimulus to provide aggregated nanoparticles;
(c) subjecting the aggregated nanoparticle to a magnetic field to provide magnetically aggregated nanoparticles; and
(d) removing the stimulus and the magnetic field to regenerate the nanoparticles, wherein the regenerated nanoparticles further comprise the diagnostic target.

In one embodiment, the stimulus is temperature.

The invention provides a method for capturing a diagnostic target, comprising:
(a) contacting a medium comprising a diagnostic target with a plurality of temperature-responsive magnetic nanoparticles, wherein each nanoparticle comprises a capture moiety reactive toward the diagnostic target;
(b) increasing the temperature of the medium to above the lower critical solution temperature of the nanoparticle to provide thermally aggregated nanoparticles;
(c) subjecting the thermally aggregated nanoparticles to a magnetic field to provide magnetically aggregated nanoparticles; and
(d) decreasing the temperature to below the lower critical solution temperature of the nanoparticle and removing the magnetic field to regenerate the nanoparticles, wherein the regenerated nanoparticles further comprise the diagnostic target.

In one embodiment, the invention provides a method for concentrating a diagnostic target, comprising:
(a) contacting a medium comprising a diagnostic target with a plurality of temperature-responsive magnetic nanoparticles, wherein each nanoparticle comprises a capture moiety reactive toward the diagnostic target;
(b) increasing temperature of the medium to above the lower critical solution temperature of the nanoparticle to provide thermally aggregated nanoparticles;
(c) subjecting the thermally aggregated nanoparticles to a magnetic field to provide magnetically aggregated nanoparticles; and
(d) decreasing the temperature to below the lower critical solution temperature of the nanoparticle and removing the magnetic field to regenerate the nanoparticles, wherein the regenerated nanoparticles further comprise the diagnostic target.

In the above methods, steps (b) to (d) may be repeated.

In another aspect, the invention also provides devices for using the stimuli-responsive nanoparticle.

In one embodiment, the invention provides a device, comprising
(a) a channel adapted for receiving a flow comprising a plurality of stimulus-responsive magnetic nanoparticles, wherein the nanoparticle is reversibly self-associative in response to a stimulus; and
(b) a separation region through which the flow passes, wherein the separation region is adapted to reversibly apply a stimulus and a magnetic field to the flow.

The invention also provides assays for using the stimuli-responsive nanoparticle.

In one embodiment, the invention provides an assay for detecting a diagnostic target, comprising:
(a) contacting the diagnostic target with a plurality of stimuli-responsive magnetic nanoparticles, wherein each nanoparticle comprises a capture moiety having affinity toward the diagnostic target;
(b) forming nanoparticle conjugates by combining the diagnostic target with the stimuli-responsive magnetic nanoparticles;
(c) aggregating the nanoparticle conjugates by applying an external stimulus;
(d) further aggregating the nanoparticle conjugates by subjecting the aggregated nanoparticle conjugates to a magnetic field;
(e) regenerating the nanoparticle conjugates by removing the stimulus and the magnetic field; and
(f) analyzing the regenerated nanoparticles comprising the diagnostic target.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 2A is a transmission electron microscope (TEM) image of the PNIPAAm mNPs. FIG. 2B is a size histogram of PNIPAAm mNPs. The images were obtained by suspending the mNPs in water and depositing onto a carbon stabilized formvar-coated copper grid. PNIPAAm was not stained, only the $\gamma$-$Fe_2O_3$ (inorganic) portion of the mNPs is visualized. The $\gamma$-$Fe_2O_3$ nanoparticles in the core exhibit a spherical shape with an average size of 4.9±0.9 nm.

FIG. 4A presents H-M measurements show that the magnetization values at a 5 T applied field were 8 and 11 emu/g for room temperature (solid) and 5 K (circle), respectively. FIG. 4B illustrates that, while the room temperature H-M measurement displays almost no hysteresis, the same measurement at 5 K shows a coercivity of 450 Oe. FIG. 4C presents T-M measurements that reveal $T_B$~25 K. ZFC and FC curves overlap above $T_B$.

DETAILED DESCRIPTION OF THE INVENTION

Figure 1:
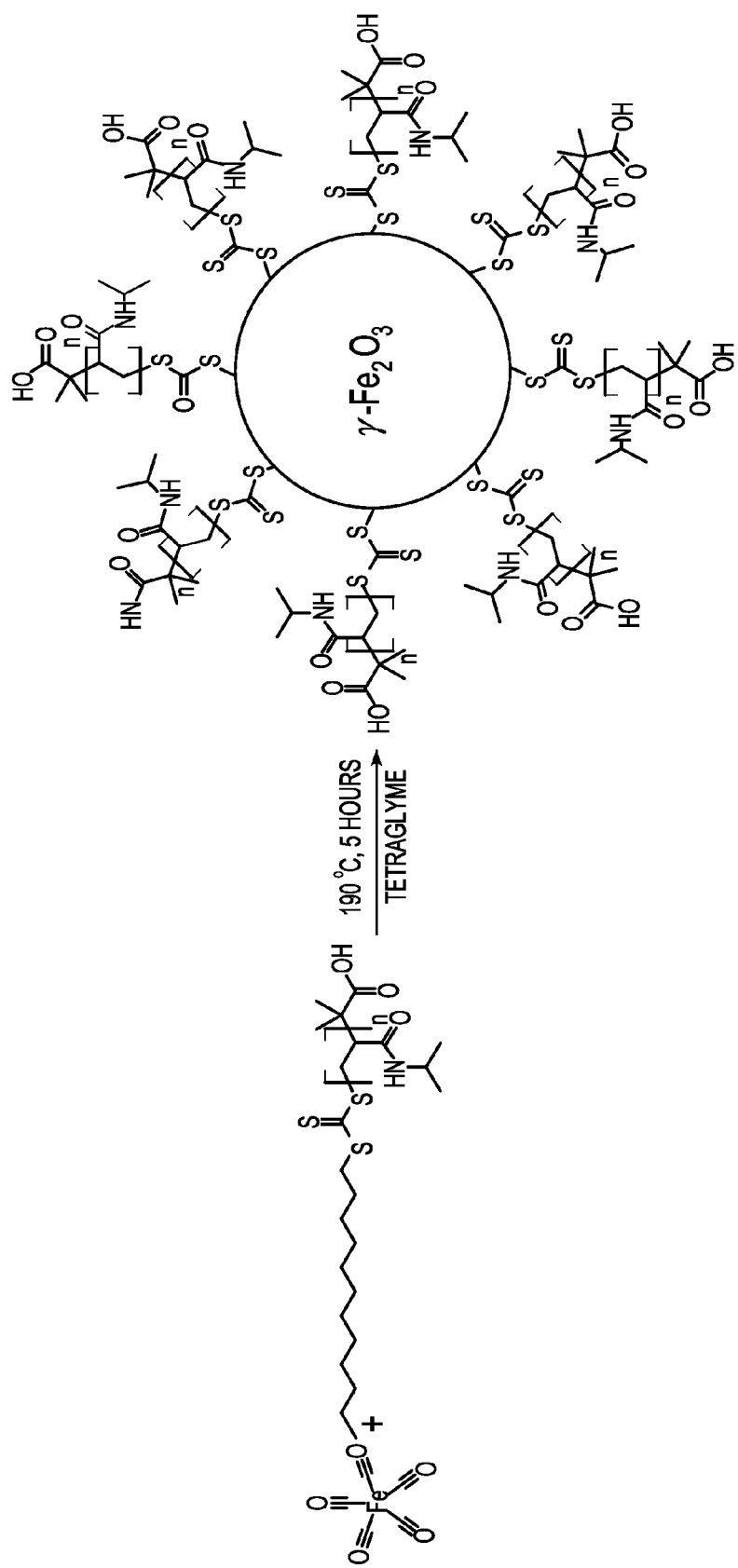
FIG. 1 is a schematic illustration of a representative method for making PNIPAAm magnetic NPs were synthesized by using PNIPAAm micelles as dimensional confinements: The reversible addition fragmentation chain transfer (RAFT) synthesized PNIPAAm chains formed micelles in tetraglyme due to the hydrophobic dodecyl group of the chain transfer agent (CTA) used in the polymerization that drives micelle assembly. The exposed chain ends on the micelle periphery (corona) is terminated with a carboxyl group that can be further functionalized. The PNIPAAm micelles were loaded with $Fe(CO)_5$ and heated at 190° C. for 5 hours to provide the $\gamma\text{-}Fe_2O_3$ cores.

The present invention provides a stimuli-responsive magnetic nanoparticle, methods of making the nanoparticles, and methods of using the nanoparticles.

Stimuli-Responsive Magnetic Nanoparticles Having Terminal Functional Groups.

In one aspect, the invention provides a stimuli-responsive magnetic nanoparticle having responsivity to a magnetic field, comprising:

(a) a core having responsivity to a magnetic field; and
(b) a plurality of stimuli-responsive polymers attached to the core, wherein the polymer terminates with a functional group capable of covalent coupling with a capture molecule.

The core includes material having responsivity to magnetic field. Suitable materials having responsivity to a magnetic field include metal oxides, such as ferrous oxide, ferric oxide, gadolinium oxide, and mixtures thereof. Mixtures of one or more metal oxide can be used. In one embodiment, the core comprises ferric oxide.

In addition to magnetic materials, the core can include non-magnetic materials, such as silicon nitride, stainless steel, titanium, and nickel titanium. Mixtures of one or more non-magnetic materials can also be used.

The core of the nanoparticles of the invention has a diameter from about 2 nm to about 10 nm. In one embodiment, the core has a diameter from about 4.0 nm to 6.0 nm.

Stimuli-Responsive Polymers.

The nanoparticles of the invention include a plurality of stimuli-responsive polymers attached to the core. In one embodiment, the plurality of stimuli-responsive polymers attached to the core forms a corona. As used herein, the term "corona" refers to the sphere or coating of stimuli-responsive polymers surrounding the core.

The stimuli-responsive polymer can be any polymer having a stimuli-responsive property. The stimuli-responsive polymer can be any one of a variety of polymers that change their associative properties (e.g., change from hydrophilic to hydrophobic) in response to a stimulus. The stimuli-responsive polymer responds to changes in external stimuli such as the pH, temperature, UV-visible light, photo-irradiation, exposure to an electric field, ionic strength, and the concentration of certain chemicals by exhibiting property change. The chemicals could be polyvalent ions such as calcium ion, polyions of either charge, or enzyme substrates such as glucose. For example, the temperature-responsive polymer is responsive to changes in temperature by exhibiting a LCST in aqueous solution. The stimuli-responsive polymer can be a multi-responsive polymer, where the polymer exhibits property change in response to combined simultaneous or sequential changes in two or more external stimuli.

The stimuli-responsive polymers may be synthetic or natural polymers that exhibit reversible conformational or physico-chemical changes such as folding/unfolding transitions, reversible precipitation behavior, or other conformational changes to in response to stimuli, such as to changes in temperature, light, pH, ions, or pressure. Representative stimuli-responsive polymers include temperature-sensitive polymers, a pH-sensitive polymers, and a light-sensitive polymers.

Stimulus-responsive polymers useful in making the nanoparticle described herein can be any which are sensitive to a stimulus that cause significant conformational changes in the polymer. Illustrative polymers described herein include temperature-, pH-, ion- and/or light-sensitive polymers. Hoffman, A. S., "Intelligent Polymers in Medicine and Biotechnology", *Artif. Organs*. 19:458-467, 1995; Chen, G. H. and A. S. Hoffman, "A New Temperature- and Ph-Responsive Copolymer for Possible Use in Protein Conjugation", *Macromol. Chem. Phys*. 196:1251-1259. 1995; Irie, M. and D. Kungwatchakun, "Photoresponsive Polymers. Mechanochemistry of Polyacrylamide Gels Having Triphenylmethane Leuco Derivatives", *Makromol. Chem., Rapid Commun.* 5:829-832, 1985; and Irie, M., "Light-induced Reversible Conformational Changes of Polymers in Solution and Gel Phase", *ACS Polym. Preprints,* 27(2):342-343, 1986; which are incorporated by reference herein.

Stimuli-responsive oligomers and polymers useful in the nanoparticle described herein can be synthesized that range in molecular weight from about 1,000 to 30,000 Daltons. In one embodiment, these syntheses are based on the chain transfer-initiated free radical polymerization of vinyl-type monomers, as described herein, and by (1) Tanaka, T., "Gels", *Sci. Amer.* 244:124-138. 1981; (2) Osada, Y. and S. B. Ross-Murphy, "Intelligent Gels", *Sci. Amer,* 268:82-87, 1993; (3) Hoffman, A. S., "Intelligent Polymers in Medicine and Biotechnology", *Artif. Organs* 19:458-467, 1995; also *Macromol. Symp.* 98:645-664, 1995; (4) Feijen, J., et al., "Thermosensitive Polymers and Hydrogels Based on N-isopropylacrylamide", 11*th European Conf. on Biomtls:* 256-260, 1994; (5) Monji, N. and A. S. Hoffman, "A Novel Immunoassay System and Bioseparation Process Based on Thermal Phase Separating Polymers", *Appl. Biochem. and Biotech.* 14:107-120, 1987; (6) Fujimura, M., T. Mori and T. Tosa, "Preparation and Properties of Soluble-Insoluble Immobilized Proteases", *Biotech. Bioeng.* 29:747-752, 1987; (7) Nguyen, A. L. and J. H. T. Luong, "Synthesis and Applications of Water-Soluble Reactive Polymers for Purification and Immobilization of Biomolecules", *Biotech. Bioeng.* 34:1186-1190, 1989; (8) Taniguchi, M., et al., "Properties of a Reversible Soluble-Insoluble Cellulase and Its Application to Repeated Hydrolysis of Crystalline Cellulose", *Biotech. Bioeng.* 34:1092-1097, 1989; (9) Monji, N., et al., "Application of a Thermally-Reversible Polymer-Antibody Conjugate in a Novel Membrane-Based Immunoassay", *Biochem. and Biophys. Res. Comm.* 172:652-660, 1990; (10) Monji, N. C. A. Cole, and A. S. Hoffman, "Activated, N-Substituted Acrylamide Polymers for Antibody Coupling: Application to a Novel Membrane-Based Immunoassay", *J. Biomtls. Sci. Polymer Ed.* 5:407-420, 1994; (11) Chen, J. P. and A. S. Hoffman, "Polymer-Protein Conjugates: Affinity Precipitation of Human IgG by Poly(N-Isopropyl Acrylamide)-Protein A Conjugates", *Biomtls.* 11:631-634, 1990; (12) Park, T. G. and A. S. Hoffman, "Synthesis and Characterization of a Soluble, Temperature-Sensitive Polymer-Conjugated Enzyme, *J. Biomtls. Sci. Polymer Ed.* 4:493-504, 1993; (13) Chen, G. H., and A. S. Hoffman, Preparation and Properties of Thermo-Reversible, Phase-Separating Enzyme-Oligo(NIPAAm) Conjugates", *Bioconj. Chem.* 4:509-514, 1993; (14) Ding, Z. L., et al., "Synthesis and Purification of Thermally-Sensitive Oligomer-Enzyme Conjugates of Poly(NIPAAm)-Trypsin", *Bioconj. Chem.* 7: 121-125, 1995; (15) Chen, G. H. and A. S. Hoffman, "A New Temperature- and pH-Responsive Copolymer for Possible Use in Protein Conjugation", *Macromol. Chem. Phys.* 196:1251-1259, 1995; (16) Takei, Y. G., et al., "Temperature-responsive Bioconjugates. 1. Synthesis of Temperature-Responsive Oligomers with Reactive End Groups and their Coupling to Biomolecules", *Bioconj. Chem.* 4:42-46, 1993; (17) Takei, Y. G., et al., "Temperature-responsive Bioconjugates. 2. Molecular Design for Temperature-modulated Bioseparations", *Bioconj. Chem.* 4:341-346, 1993; (18) Takei, Y. G., et al., "Temperature-responsive Bioconjugates. 3. Antibody-Poly(N-isopropylacrylamide) Conjugates for Temperature-Modulated Precipitations and Affinity Bioseparations", *Bioconj. Chem.* 5:577-582, 1994; (19) Matsukata, M., et al., "Temperature Modulated Solubility-Activity Alterations for Poly(N-Isopropylacrylamide)-Lipase Conjugates", *J. Biochem.* 116:682-686, 1994; (20) Chilkoti, A., et al., "Site-Specific Conjugation of a Temperature-Sensitive Polymer to a Genetically-Engineered Protein", *Bioconj. Chem.* 5:504-507, 1994; and (21) Stayton, P. S., et al., "Control of Protein-Ligand Recognition Using a Stimuli-Responsive Polymer", *Nature* 378:472-474, 1995.

The stimuli-responsive polymers useful in the nanoparticles of the invention include homopolymers and copolymers having stimuli-responsive behavior. Other suitable stimuli-responsive polymers include block and graft copolymers having one or more stimuli-responsive polymer components. A suitable stimuli-responsive block copolymer may include, for example, a temperature-sensitive polymer block, or a pH-sensitive block. A suitable stimuli-responsive graft copolymer may include, for example, a pH-sensitive polymer backbone and pendant temperature-sensitive polymer components, or a temperature-sensitive polymer backbone and pendant pH-sensitive polymer components.

The stimuli-responsive polymer can include a polymer having a balance of hydrophilic and hydrophobic groups, such as polymers and copolymers of N-isopropylacrylamide. An appropriate hydrophilic/hydrophobic balance in a smart vinyl type polymer is achieved, for example, with a pendant hydrophobic group of about 2-6 carbons that hydrophobically bond with water, and a pendant polar group such as an amide, acid, amine, or hydroxyl group that H-bond with water. Other polar groups include sulfonate, sulfate, phosphate and ammonium ionic groups. Preferred embodiments are for 3-4 carbons (e.g., propyl, isopropyl, n-butyl, isobutyl, and t-butyl) combined with an amide group (e.g. PNIPAAm), or 2-4 carbons (e.g., ethyl, propyl, isopropyl, n-butyl, isobutyl, and t-butyl) combined with a carboxylic acid group (e.g., PPAA). There is also a family of smart A-B-A (also A-B-C) block copolymers of polyethers, such as PLURONIC polymers having compositions of PEO-PPO-PEO, or polyester-ether compositions such as PLGA-PEG-PLGA. In one embodiment, the stimuli-responsive polymer is a temperature responsive polymer, poly(N-isopropylacrylamide) (PNIPAAm).

The stimuli-responsive polymer useful in the invention can be a smart polymer having different or multiple stimuli-responsivities, such as homopolymers responsive to pH or light. Block, graft, or random copolymers with dual sensitivities, such as pH and temperature, light and temperature, or pH and light, may also be used.

The stimuli-responsive polymer can contain a micelle-forming hydrophobic moiety. The hydrophobic group can be a saturated or unsaturated alkyl group, a hydrophobic oligomer or polymer such as a polyester, polyamide or polypeptide, any one of which could be incorporated as a block in a block copolymer, or a pendant graft polymer in a graft copolymer. In one embodiment, the micelle-forming hydrophobic moiety is an alkyl group. In one embodiment, the micelle-forming hydrophobic moiety is a n-dodecyl group.

Temperature-Sensitive Polymers.

Illustrative embodiments of the many different types of temperature-sensitive polymers that may be conjugated to interactive molecules are polymers and copolymers of N-isopropyl acrylamide (NIPAAm). PolyNIPAAm is a thermally sensitive polymer that precipitates out of water at 32° C., which is its lower critical solution temperature (LCST), or cloud point (Heskins and Guillet, *J. Macromol. Sci.-Chem. A*2:1441-1455, 1968). When polyNIPAAm is copolymerized with more hydrophilic comonomers such as acrylamide, the LCST is raised. The opposite occurs when it is copolymerized with more hydrophobic comonomers, such as N-t-butyl acrylamide. Copolymers of NIPAAm with more hydrophilic monomers, such as AAm, have a higher LCST, and a broader temperature range of precipitation, while copolymers with more hydrophobic monomers, such as N-t-butyl acrylamide, have a lower LCST and usually are more likely to retain the sharp transition characteristic of PNIPAAm (Taylor and Cerankowski, *J. Polymer Sci.* 13:2551-2570, 1975; Priest et al., *ACS Symposium Series* 350:255-264, 1987; and Heskins and Guillet, *J. Macromol. Sci.-Chem. A*2:1441-1455, 1968, the disclosures of which are incorporated herein). Copolymers can be produced having higher or lower LCSTs and a broader temperature range of precipitation.

The synthesis of an amino-terminated polymer proceeds by the radical polymerization of NIPAAm in the presence of AIBN as an initiator and 1-aminoethanethiol-hydrochloride as a chain transfer reagent. To synthesize a chain with —COOH or —OH terminal groups, carboxyl- or hydroxyl-thiol chain transfer agents, respectively, have been used instead of the amino-thiol. It should be noted that the synthesis of the end-reactive polymers is based on a chain transfer initiation and termination mechanism. This yields a relatively short polymer chain, having a molecular weight somewhere between 1000 and 25,000 to 30,000. The shortest chains, less than 10,000 in molecular weight, are usually called "oligomers." Oligomers of different molecular weights can be synthesized by simply changing the ratio of monomer to chain transfer reagent, and controlling their concentration levels, along with that of the initiator. The polymers useful in the invention may also be prepared by reversible addition fragmentation chain transfer (RAFT) polymerization.

Oligomers of NIPAAm (or other vinyl monomers) having a reactive group at one end are prepared by the radical polymerization of NIPAAm using AIBN as initiator, plus a chain transfer agent with a thiol (—SH) group at one end and the desired "reactive" group (e.g., —OH, —COOH, —$NH_2$) at the other end. Chen and Hoffman, *Bioconjugate Chem.* 4:509-514, 1993 and Chen and Hoffman, *J. Biomaterials Sci. Polymer Ed.* 5:371-382, 1994, each of which is incorporated herein by reference. Appropriate quantities of NIPAAm, AIBN and chain transfer reagent in DMF are placed in a thick-walled polymerization tube and the mixtures are degassed by freezing and evacuating and then thawing (4 times). After cooling for the last time, the tubes are evacuated and sealed prior to polymerization. The tubes are immersed in a water bath at 60° C. for 4 h. The resulting polymer is isolated by precipitation into diethyl ether and weighed to determine yield. The molecular weight of the polymer is determined either by titration (if the end group is amine or carboxyl), by vapor phase osmometry (VPO), or gel permeation chromatography (GPC).

Temperature sensitive oligopeptides also may be incorporated into the nanoparticles.

pH-Sensitive Polymers.

Synthetic pH-sensitive polymers useful in making the nanoparticles described herein are typically based on pH-sensitive vinyl monomers, such as acrylic acid (AAc), methacrylic acid (MAAc) and other alkyl-substituted acrylic acids such as ethylacrylic acid (EAAc), propylacrylic acid (PAAc), and butylacrylic acid (BAAc), maleic anhydride (MAnh), maleic acid (MAc), AMPS (2-acrylamido-2-methyl-1-propanesulfonic acid), N-vinyl formamide (NVA), N-vinyl acetamide (NVA) (the last two may be hydrolyzed to polyvinylamine after polymerization), aminoethyl methacrylate (AEMA), phosphoryl ethyl acrylate (PEA) or methacrylate (PEMA). pH-Sensitive polymers may also be synthesized as polypeptides from amino acids (e.g., polylysine or polyglutamic acid) or derived from naturally-occurring polymers such as proteins (e.g., lysozyme, albumin, casein), or polysaccharides (e.g., alginic acid, hyaluronic acid, carrageenan, chitosan, carboxymethyl cellulose) or nucleic acids, such as DNA. pH-Responsive polymers usually contain pendant pH-sensitive groups such as —$OPO(OH)_2$, —COOH, or —$NH_2$ groups. With pH-responsive polymers, small changes in pH can stimulate phase-separation, similar to the effect of temperature on solutions of PNIPAAm (Fujimura et al. *Biotech. Bioeng.* 29:747-752 (1987)). By randomly copolymerizing a thermally-sensitive NIPAAm with a small amount (e.g., less than 10 mole percent) of a pH-sensitive comonomer such as AAc, a copolymer will display both temperature and pH sensitivity. Its LCST will be almost unaffected, sometimes even lowered a few degrees, at pHs where the comonomer is not ionized, but it will be dramatically raised if the pH-sensitive groups are ionized. When the pH-sensitive monomer is present in a higher content, the LCST response of the temperature sensitive component may be "eliminated" (e.g., no phase separation seen up to and above 100° C.).

Graft and block copolymers of pH and temperature sensitive monomers can be synthesized that retain both pH and temperature transitions independently. Chen, G. H., and A. S. Hoffman, *Nature* 373:49-52, 1995. For example, a block copolymer having a pH-sensitive block (polyacrylic acid) and a temperature sensitive block (PNIPAAm) can be useful in the invention.

Light-Sensitive Polymers.

Light-responsive polymers usually contain chromophoric groups pendant to or along the main chain of the polymer and, when exposed to an appropriate wavelength of light, can be isomerized from the trans to the cis form, which is dipolar and more hydrophilic and can cause reversible polymer conformational changes. Other light sensitive compounds can also be converted by light stimulation from a relatively non-polar hydrophobic, non-ionized state to a hydrophilic, ionic state.

In the case of pendant light-sensitive group polymers, the light-sensitive dye, such as aromatic azo compounds or stilbene derivatives, may be conjugated to a reactive monomer (an exception is a dye such as chlorophyllin, which already has a vinyl group) and then homopolymerized or copolymerized with other conventional monomers, or copolymerized with temperature-sensitive or pH-sensitive monomers using the chain transfer polymerization as described above. The light sensitive group may also be conjugated to one end of a different (e.g., temperature) responsive polymer. A number of protocols for such dye-conjugated monomer syntheses are known.

Although both pendant and main chain light sensitive polymers may be synthesized and are useful for the methods and applications described herein, the preferred light-sensitive polymers and copolymers thereof are typically synthesized from vinyl monomers that contain light-sensitive pendant groups. Copolymers of these types of monomers are prepared with "normal" water-soluble comonomers such as acrylamide, and also with temperature- or pH-sensitive comonomers such as NIPAAm or AAc.

Light-sensitive compounds may be dye molecules that isomerize or become ionized when they absorb certain wavelengths of light, converting them from hydrophobic to hydrophilic conformations, or they may be other dye molecules which give off heat when they absorb certain wavelengths of light. In the former case, the isomerization alone can cause chain expansion or collapse, while in the latter case the polymer will precipitate only if it is also temperature-sensitive.

Light-responsive polymers usually contain chromophoric groups pendant to the main chain of the polymer. Typical chromophoric groups that have been used are the aromatic diazo dyes (Ciardelli, *Biopolymers* 23:1423-1437, 1984; Kungwatchakun and Irie, *Makromol. Chem., Rapid Commun.*

9:243-246, 1988; Lohmann and Petrak, *CRC Crit. Rev. Therap. Drug Carrier Systems* 5:263, 1989; Mamada et al., *Macromolecules* 23:1517, 1990, each of which is incorporated herein by reference). When this type of dye is exposed to 350-410 nm UV light, the trans form of the aromatic diazo dye, which is more hydrophobic, is isomerized to the cis form, which is dipolar and more hydrophilic, and this can cause polymer conformational changes, causing a turbid polymer solution to clear, depending on the degree of dye-conjugation to the backbone and the water solubility of the main unit of the backbone. Exposure to about 750 nm visible light will reverse the phenomenon. Such light-sensitive dyes may also be incorporated along the main chain of the backbone, such that the conformational changes due to light-induced isomerization of the dye will cause polymer chain conformational changes. Conversion of the pendant dye to a hydrophilic or hydrophobic state can also cause individual chains to expand or contract their conformations. When the polymer main chain contains light sensitive groups (e.g., azo benzene dye) the light-stimulated state may actually contract and become more hydrophilic upon light-induced isomerization. The light-sensitive polymers can include polymers having pendant or backbone azobenzene groups.

Specific Ion-Sensitive Polymers.

Polysaccharides, such as carrageenan, that change their conformation, for example, from a random to an ordered conformation, as a function of exposure to specific ions, such as potassium or calcium, can also be used as the stimulus-responsive polymers. In another example, a solution of sodium alginate may be gelled by exposure to calcium. Other specific ion-sensitive polymers include polymers with pendant ion chelating groups, such as histidine or EDTA.

Dual- or Multi-Sensitivity Polymers.

If a light-sensitive polymer is also thermally-sensitive, the UV- or visible light-stimulated conversion of a chromophore conjugated along the backbone to a more hydrophobic or hydrophilic conformation can also stimulate the dissolution or precipitation of the copolymer, depending on the polymer composition and the temperature. If the dye absorbs the light and converts it to thermal energies rather than stimulating isomerization, then the localized heating can also stimulate a phase change in a temperature-sensitive polymer such as PNIPAAm, when the system temperature is near the phase separation temperature. The ability to incorporate multiple sensitivities, such as temperature and light sensitivity, or temperature and pH sensitivity, along one backbone by vinyl monomer copolymerization lends great versatility to the synthesis and properties of the responsive polymer-protein conjugates. For example, dyes can be used which bind to protein recognition sites, and light-induced isomerization can cause loosening or detachment of the dye from the binding pocket (Bieth et al., *Proc. Natl. Acad. Sci. USA* 64:1103-1106, 1969). This can be used for manipulating affinity processes by conjugating the dye to the free end of a temperature responsive polymer, such as ethylene oxide-propylene oxide (EO-PO) random copolymers available from Carbide. These polymers, —$(CH_2CH_2O)_x$—$(CH_2CHCH_3O)_y$—, have two reactive end groups. The phase separation point (cloud point) can be varied over a wide range, depending on the EO/PO ratio, molecular weight, and concentration, and one end may be derivatized with the ligand dye and the other end with an —SH reactive group, such as vinyl sulfone (VS).

Binding Pairs.

In one embodiment, the stimuli-responsive magnetic particles include polymers having terminal functional groups for covalently coupling a capture molecule. The terminal functional group on the stimuli-responsive polymer refers to any reactable group that may be derivatized to make it reactive with the capture moiety, such as carboxyl, hydroxyl, and amine groups. The terminal functional group may be derivatized to form reactive groups such as thiol, ketone, N-hydroxy succinimide esters, N-hydroxy maleimide esters, carbonyl imidazoles, carbodiimide esters, vinyl sulfone, acrylate, benzyl halide, tosylate, tresylate, aldehyde, hydrazone, acid halide, p-nitrophenolic esters, and hydroperoxides. In one embodiment, the terminal functional group on the stimuli-responsive polymer is a carboxylic group.

The terminal functional group on the stimuli-responsive polymer can be coupled with a capture molecule through covalent bonds, including but not limited to amide, esters, ether, thioether, disulfide, hydrazide, hydrazone, acetal, ketal, ketone, anhydride, urethane, urea, and carbamate bonds. In one embodiment, the biotin moiety is coupled to the stimuli-responsive polymer through an amide bond.

The terminal functional group can be covalently coupled to a capture molecule, such as a protein, a nucleic acid oligomer (DNA or RNA), an antibody, an antigen, an enzyme or an enzyme substrate. The capture moiety can be further coupled with a target molecule, such as a protein, a nucleic acid oligomer (DNA or RNA), an antigen, an antibody, an enzyme, or an enzyme substrate through covalent or non-covalent interaction. In one embodiment, the terminal functional group is coupled to a biotin, the capture molecule, to afford a biotinylated nanoparticle. In one embodiment, the biotinylated nanoparticle can be further conjugated to a streptavidin, the target molecule, to yield a streptavidin-conjugated biotinylated nanoparticle, that can be coupled to a biotinylated target molecule.

A capture molecule and a target molecule form a binding pair. Each has an affinity toward the other (e.g., antigen and antibody). Each of the capture molecule and the target molecule can be a variety of different molecules, including peptides, proteins, poly- or oligosaccharides, glycoproteins, lipids and lipoproteins, and nucleic acids, as well as synthetic organic or inorganic molecules having a defined bioactivity, such as an antibiotic or anti-inflammatory agent, that binds to a target site, such as a cell membrane receptor. The exemplary proteins include antibodies (monoclonal, polyclonal, chimeric, single-chain or other recombinant forms), their protein/peptide antigens, protein/peptide hormones, streptavidin, avidin, protein A, protein G, growth factors and their respective receptors, DNA-binding proteins, cell membrane receptors, endosomal membrane receptors, nuclear membrane receptors, neuron receptors, visual receptors, and muscle cell receptors. Exemplary oligonucleotides include DNA (genomic or cDNA), RNA, antisense, ribozymes, and external guide sequences for RNAase P, and can range in size from short oligonucleotide primers up to entire genes. Carbohydrates include tumor associated carbohydrates (e.g., $Le^x$, sialyl $Le^x$, $Le^y$, and others identified as tumor associated as described in U.S. Pat. No. 4,971,905, incorporated herein by reference), carbohydrates associated with cell adhesion receptors (e.g., Phillips et al., *Science* 250:1130-1132, 1990), and other specific carbohydrate binding molecules and mimetics thereof which are specific for cell membrane receptors.

Among the proteins, streptavidin is particularly useful as a model for other capture moiety-target molecule binding pair systems described herein. Streptavidin is an important component in many separations and diagnostic technologies which use the very strong association of the streptavidin-biotin affinity complex. (Wilchek and Bayer, Avidin-Biotin Technology, New York, Academic Press, Inc., 1990; and Green, *Meth. Enzymol.* 184:51-67. Protein G, a protein that binds IgG antibodies (Achari et al., *Biochemistry* 31:10449-10457, 1992, and Akerstrom and Bjorck, *J. Biol. Chem.* 261: 10240-10247, 1986) is also useful as a model system. Representative immunoaffinity molecules include engineered single chain Fv antibody (Bird et al., *Science* 242:423-426, 1988 and U.S. Pat. No. 4,946,778 to Ladner et al., incorporated herein by reference, Fab, Fab', and monoclonal or polyclonal antibodies.

In one embodiment, the capture molecule is an antibody and the target molecule is an antigen. In another embodiment, both the capture molecule and the target molecule are protein. In another embodiment, the capture molecule is a nucleic acid (DNA or RNA) and the target molecule is a complimentary nucleic acid (DNA or RNA). In another embodiment, the target molecule is a nucleic acid (DNA or RNA) and the capture molecule is a protein. In another embodiment, the capture molecule is a cell membrane receptors and the target molecule is a ligand. In another embodiment, the capture moiety is an enzyme and the target molecule is a substrate. In another embodiment, the capture molecule is biotin and the target molecule is streptavidin or avidin. In another embodiment, the target moiety is a cell (e.g., a living cell).

Stimuli-Responsive Magnetic Nanoparticles Having Capture Moieties.

In one aspect, the invention provides a stimuli-responsive magnetic nanoparticle, comprising:
(a) a core having responsivity to a magnetic field; and
(b) a plurality of stimuli-responsive polymers attached to the core, wherein the polymer terminates with a capture moiety.

In one embodiment, the capture moiety is an antibody. In one embodiment, the capture moiety is an antigen. In one embodiment, the capture moiety is a nucleic acid oligomer (DNA or RNA). In one embodiment, the capture moiety is an enzyme substrate. In one embodiment, the capture moiety is biotin.

In one embodiment, the capture moiety is a biotin or biotin derivative having affinity to avidin or streptavidin. In this embodiment, the nanoparticle includes a plurality of biotin moieties coupled to the stimuli-responsive polymer. In one embodiment, the biotin or derivative is coupled to the polymer through an amide bond. In one embodiment, the nanoparticles of the invention have from about 50 to about 100 biotin moieties/nanoparticle. In one embodiment, the nanoparticle is further coupled to streptavidin molecules via biotin moieties. In one embodiment, the nanoparticle has from about 30 to about 70 streptavidins/nanoparticle.

Nanoparticle Properties.

The nanoparticles of the invention may have diameters of from about 3 nm to about 70 nm. In one embodiment, the nanoparticles have diameters from about 5 nm to about 30 nm. In one embodiment, the nanoparticles have diameters from about 5 nm to about 10 nm. In one embodiment, the nanoparticles have diameters from about 4 nm to about 6 nm.

As used herein, "mNP" refers to magnetic nanoparticle; "PNIPAAm mNP" refers to poly(N-isopropylacrylamide) magnetic nanoparticle; "bPNIPAAm mNP" refers to biotinylated poly(N-isopropylacrylamide) magnetic nanoparticle; and "SA-bPNIPAAm mNP" refers to biotinylated poly(N-isopropylacrylamide) magnetic nanoparticle conjugated with streptavidin.

Figure 2A:
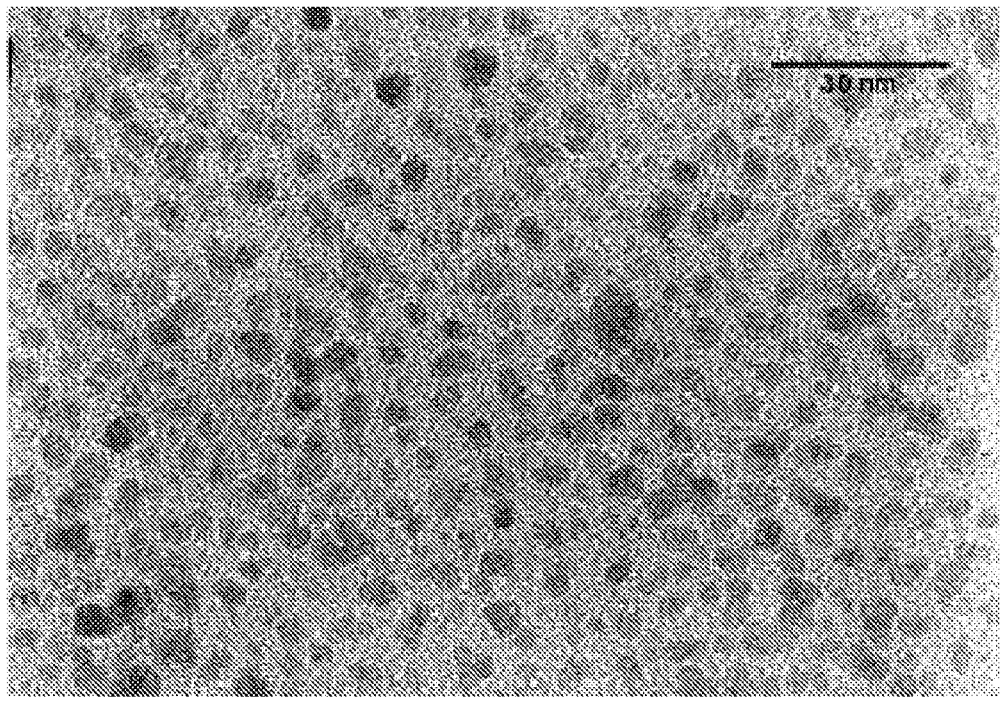
FIGS. 2A and 2B illustrate representative PNIPAAm mNPs of the invention.
Figure 2B:
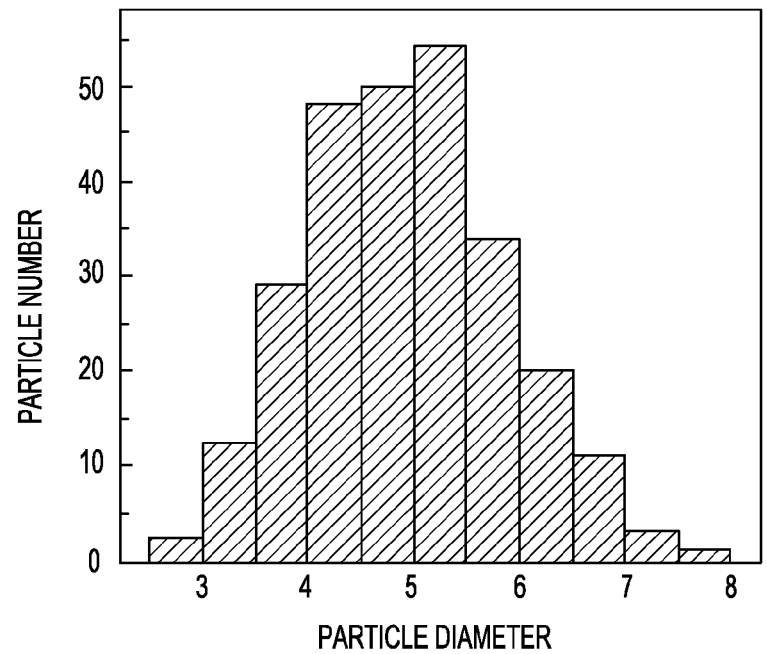
Figure 3:
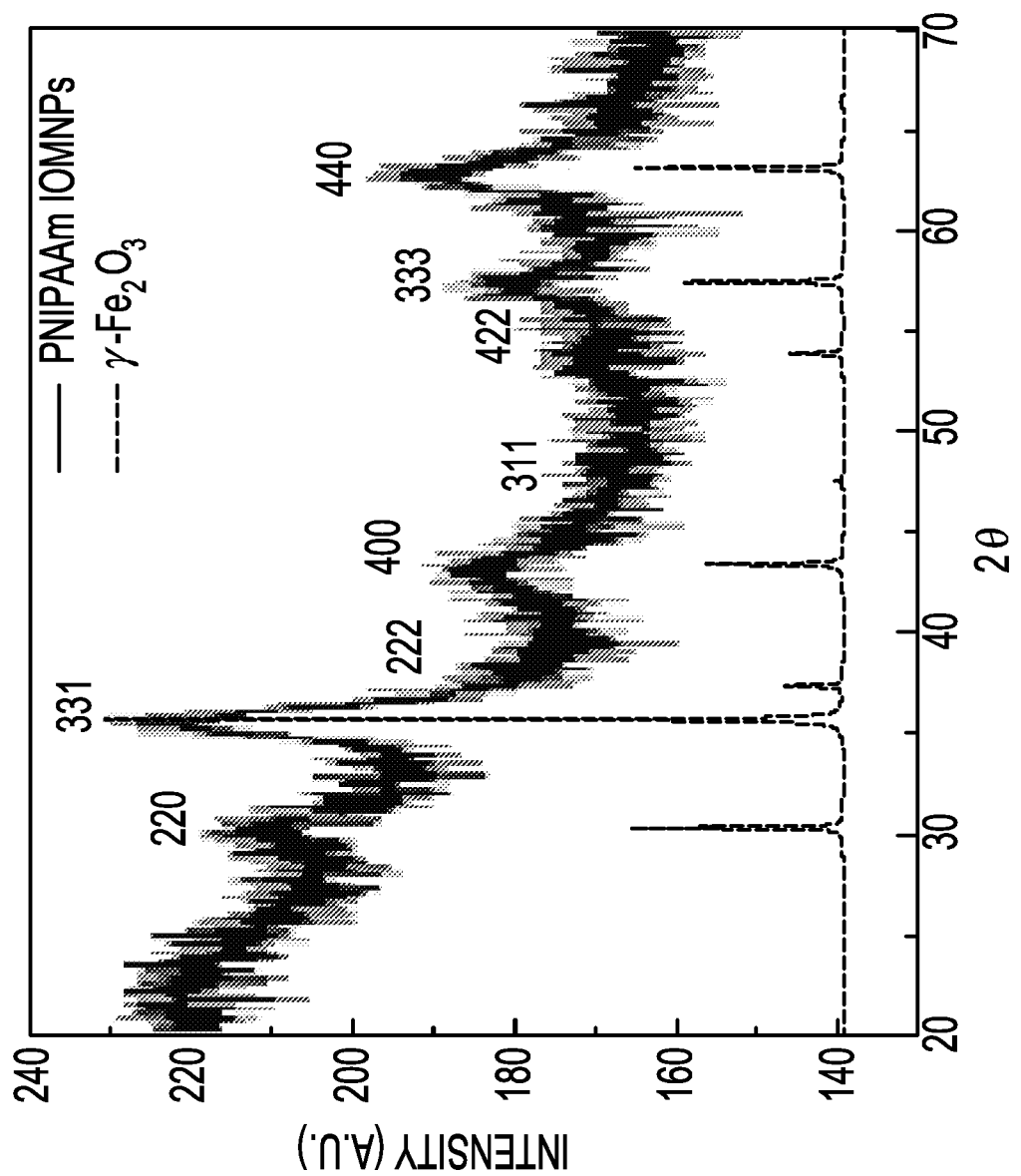
FIG. 3 is an X-ray diffraction (XRD) pattern of representative PNIPAAm mNPs of the invention (solid) that matches the theoretical $\gamma$-$Fe_2O_3$ (dashed) index. The broadened pattern for the PNIPAAm mNPs reflects their polycrystalline nature.

The characterization of representative stimuli-responsive mNPs, PNIPAAm mNPs, were carried out by transmission electron microscopy (TEM) and dynamic light scattering (DLS) analysis. The TEM images and resulting size histograms are shown in FIGS. 2A and 2B, respectively. Only the $\gamma$-$Fe_2O_3$ (inorganic) portion of the mNPs was visualized, the PNIPAAm is not stained. The inorganic portion of the particles exhibits a spherical shape with an average size of 4.9±0.9 nm. The number averaged particle diameter from a multimodal DLS size distribution was 6.7±2.7 nm for the PNIPAAm mNP, and 11.5±1.7 nm for the bPNIPAAm mNP. The crystal structure of mNPs was characterized by X-ray diffraction (XRD) analysis (FIG. 3). The XRD pattern of the PNIPAAm mNPs (solid) matches the theoretical $\gamma$-$Fe_2O_3$ (dashed) spectrum. The broadened pattern for the PNIPAAm mNPs reflects their polycrystalline nature.

Figure 4A:
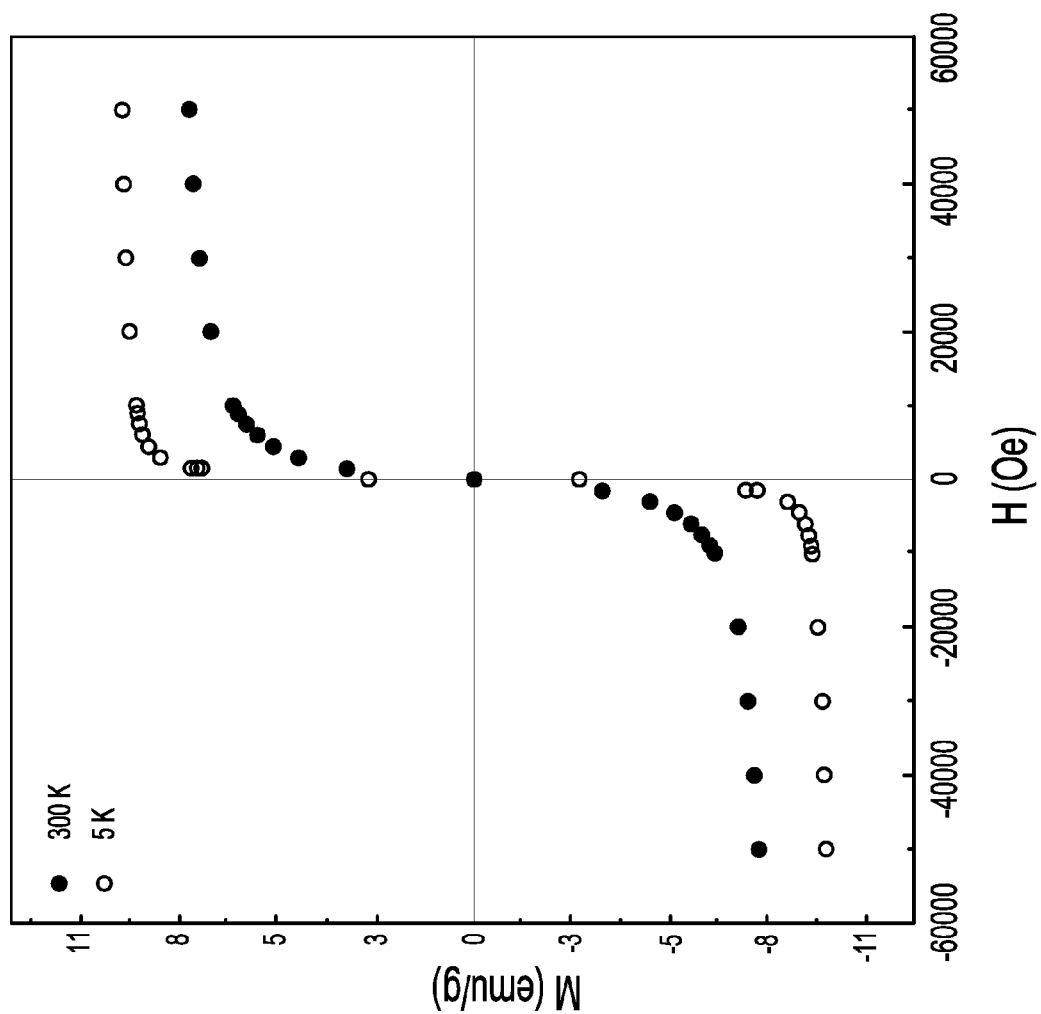
FIGS. 4A-4C present magnetic properties for representative PNIPAAm mNPs of the invention.
Figure 4B:
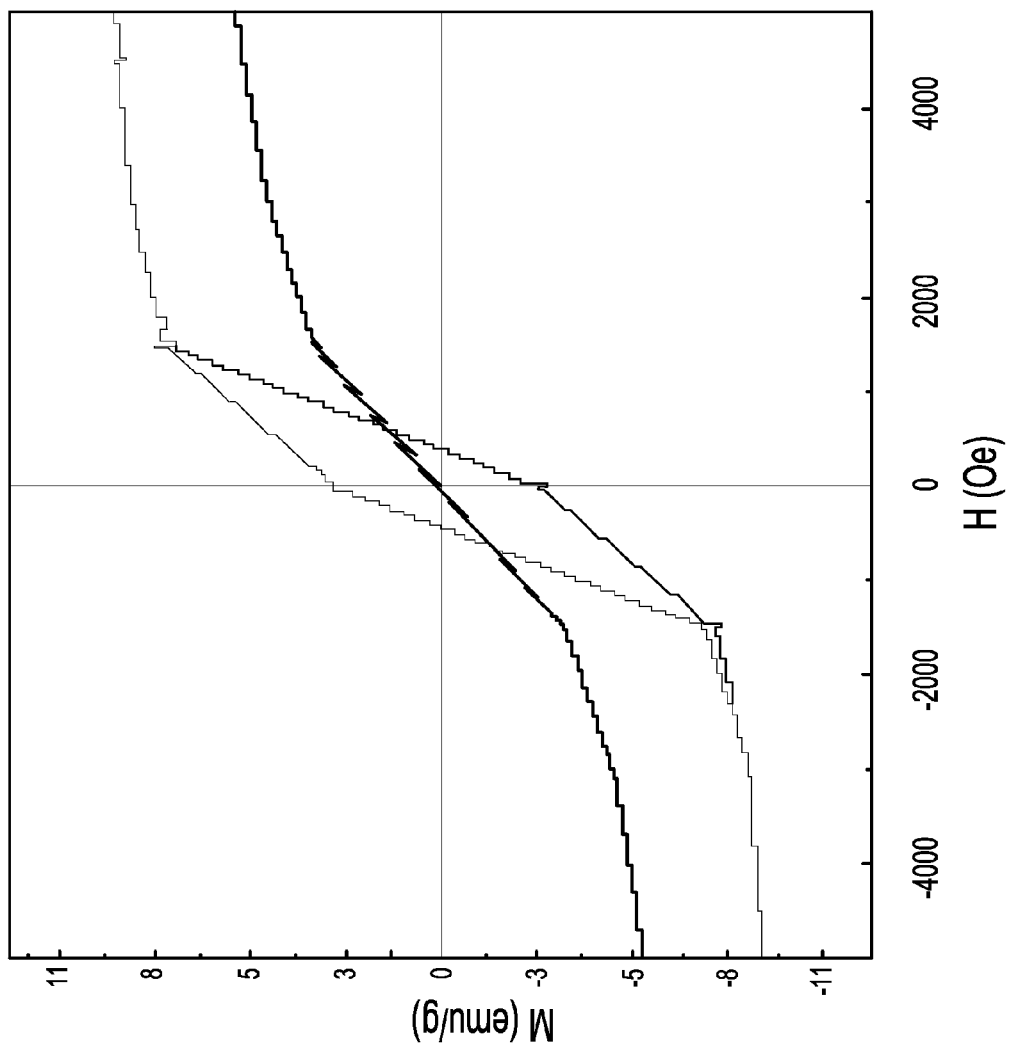
Figure 4C:
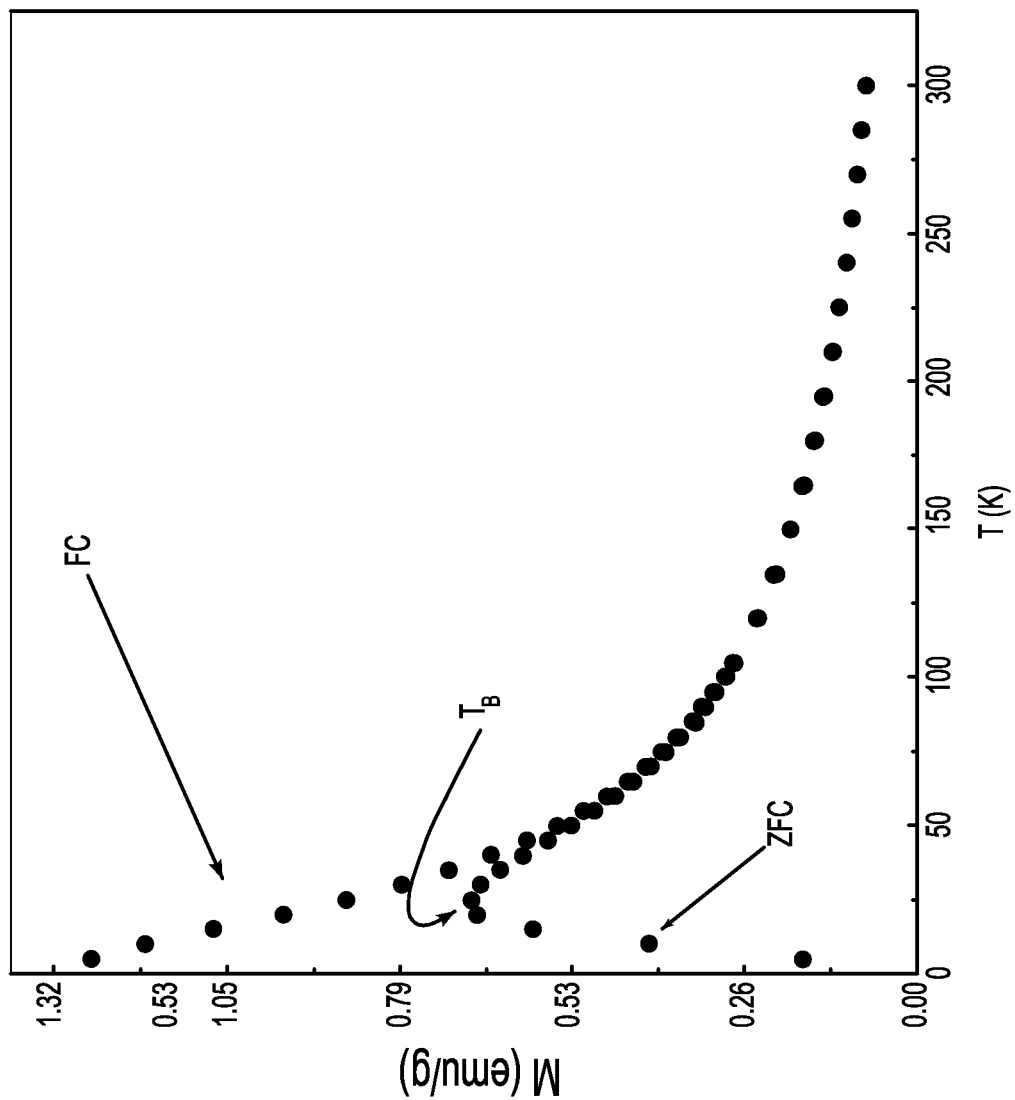

The magnetic properties of the exemplary temperature responsive mNPs, PNIPAAm mNP, were characterized with a Superconducting Quantum Interference Device (SQUID) at a field range of ±5 T (field vs. magnetization, H-M) and a temperature range from 5 to 300 K (temperature vs. magnetization, T-M). H-M measurements (FIG. 4A) were used to ascertain the induced magnetization from the nanoparticles at the applied field. Magnetization values at a 5 T applied field were 8 and 11 emu/g for room temperature and 5 K, respectively. While the room temperature H-M measurement displays almost no hysteresis, the same measurement at 5 K (FIG. 4aB) shows a coercivity of 450 Oe. The T-M measurement (FIG. 4C) shows a blocking temperature, $T_B$, of 25 K. Zero-field-cooled (ZFC) and field-cooled (FC) curves overlap above $T_B$, which can be correlated to the size distribution. The results of the SQUID measurements confirm these PNIPAAm modified mNPs are superparamagnetic.

Methods for Making Stimuli-Responsive Nanoparticles.

In another aspect, the invention provides a method for making stimuli-responsive nanoparticles.

In one embodiment, the stimuli-responsive nanoparticles are made by the following steps:
(a) providing a plurality of stimuli-responsive polymers to form a micelle having a hydrophobic core; and
(b) loading the hydrophobic core with material having responsivity to a magnetic field.

In the above method, the hydrophobic core formed by the micelle can be used as dimensional confinement to synthesize a core having responsivity to a magnetic field.

In one embodiment, the stimuli-responsive mNPs are temperature-responsive mNPs. The temperature-responsive mNPs can be synthesized from temperature-responsive polymeric micelles. In one embodiment, telechelic poly(N-isopropylacrylamide) (PNIPAAm) polymer chains were synthesized with dodecyl tails at one end and a reactive carboxylate at the opposite end by the reversible addition fragmentation chain transfer (RAFT) technique. These PNIPAAm chains self-associate into micelles that were used as dimensional confinements to synthesize the magnetic nanoparticles. The resulting superparamagnetic nanoparticles exhibit a $\gamma$-$Fe_2O_3$ core (~5 nm) with a layer of carboxylate-terminated PNIPAAm on the surface. The carboxylate-group was used to functionalize the magnetic nanoparticles with biotin and subsequently streptavidin.

The PNIPAAm mNPs described above were synthesized in one-step with a polymeric micelle approach that was utilized to take advantage of the RAFT synthesis technique (FIG. 1). The PNIPAAm chains were synthesized from a RAFT chain transfer agent (CTA) that contains a hydrophobic dodecyl group at one end and a carboxyl group at the other end. These chains formed micelles in tetraglyme solvent, driven by the association of the core-forming dodecyl groups. The polydispersity index of the RAFT-synthesized PNIPAAm was less than 1.10, which correspondingly yielded micelles with narrow size dispersities (hydrodynamic diameter of 27 nm with 13.5 nm half-widths at maximum intensity). The PNIPAAm micelles were loaded with the iron oxide reactants, where the micelles served as dimensional confinements for the synthesis of thermal responsive iron oxide mNPs. The telechelic nature of the RAFT-synthesized chain ends in the exposed PNIPAAm coating layer could be readily exploited to subsequently conjugate biotin groups via the solvent-exposed end carboxyl groups. The biotinylated particles (bPNIPAAm mNPs) were complexed with streptavidin (SA) as SA-bPNIPAAm mNPs. The HABA assay was used to quantify the number of biotins and SA, with a result of 89 biotins per bPNIPAAm mNP and 46 SA per bPNIPAAm mNP.

Methods for Using the Stimuli-Responsive Nanoparticles.

In other aspects, the invention provides methods for using the nanoparticle.

In one embodiment, the invention provides a method for capturing a diagnostic target, comprising:
(a) contacting a medium comprising a diagnostic target with a plurality of stimuli-responsive magnetic nanoparticles, wherein each nanoparticle comprises a capture moiety reactive toward the diagnostic target;
(b) applying an external stimulus to provide aggregated nanoparticles;
(c) subjecting the aggregated nanoparticle to a magnetic field to provide magnetically aggregated nanoparticles; and
(d) removing the stimulus and the magnetic field to regenerate the nanoparticles, wherein the regenerated nanoparticles further comprise the diagnostic target.

In the above methods, the external stimulus could be temperature, pH, or light. In one embodiment the stimuli-responsive magnetic nanoparticle is a pH-responsive nanoparticle, and the external stimulus is the pH. In one embodiment the stimuli-responsive magnetic nanoparticle is a light-responsive nanoparticle, and the external stimulus is light. In one embodiment the stimuli-responsive magnetic nanoparticle is ion-responsive nanoparticle, and the external stimulus is the ion strength of a specific ion.

In one embodiment, the stimulus is temperature. The invention provides a method for capturing a diagnostic target, comprising:
(a) contacting a medium comprising a diagnostic target with a plurality of temperature-responsive magnetic nanoparticles, wherein each nanoparticle comprises a capture moiety reactive toward the diagnostic target;
(b) increasing the temperature of the medium to above the lower critical solution temperature of the nanoparticle to provide thermally aggregated nanoparticles;
(c) subjecting the thermally aggregated nanoparticles to a magnetic field to provide magnetically aggregated nanoparticles; and
(d) decreasing the temperature to below the lower critical solution temperature of the nanoparticle and removing the magnetic field to regenerate the nanoparticles, wherein the regenerated nanoparticles further comprise the diagnostic target.

In one embodiment, the invention provides a method for concentrating a diagnostic target, comprising:
(a) contacting a medium comprising a diagnostic target with a plurality of temperature-responsive magnetic nanoparticles, wherein each nanoparticle comprises a capture moiety reactive toward the diagnostic target;
(b) increasing temperature of the medium to above the lower critical solution temperature of the nanoparticle to provide thermally aggregated nanoparticles;
(c) subjecting the thermally aggregated nanoparticles to a magnetic field to provide magnetically aggregated nanoparticles; and
(d) decreasing the temperature to below the lower critical solution temperature of the nanoparticle and removing the magnetic field to regenerate the nanoparticles, wherein the regenerated nanoparticles further comprise the diagnostic target.

In the above methods, steps (b) to (d) may be repeated.

In the above methods, the diagnostic target molecule and the capture moiety each has affinity toward the other and are capable of forming a binding pair. As used herein, the term "diagnostic target" refers to a molecule that is indicative of a diseased condition or an indicator of exposure to a toxin, or a therapeutic drug that has been administered to a subject and whose concentration is to be monitored.

In one embodiment, the diagnostic target molecule is an antibody and the capture moiety is an antigen. In one embodiment, the diagnostic target molecule is an antigen and the capture moiety is an antibody. In one embodiment, the diagnostic target molecule is a nucleic acid oligomer (RNA or DNA) and the capture moiety is a complementary nucleic acid oligomer. In one embodiment, the diagnostic target molecule is a nucleic acid oligomer (RNA or DNA) and the capture moiety is a protein. In one embodiment, the diagnostic target molecule is a protein and the capture moiety is a nucleic acid oligomer (RNA or DNA). In one embodiment, the diagnostic target molecule is an enzyme and the capture moiety is a substrate. In one embodiment, the diagnostic target molecule is an enzyme substrate and the capture moiety is an enzyme.

In one embodiment, the methods can be carried out in point-of-care microfluidic devices. In one embodiment, the methods can be carried out in the microfluidic channel settings. In one embodiment, the methods can be carried out in microfluidic lab card settings.

The dual magneto- and thermally-responsive mNPs of the invention are designed to facilitate diagnostic target isolation and/or assay. The temperature responsive mNPs reversibly aggregate as the temperature is cycled above and below the LCST. Aggregation of the mNPs results in an increase of the effective particle size, facilitating the magnetic separation of the particles to the channels walls out of the flow stream with a small applied field. As the temperature is reversed below the LCST and the applied field is removed, the captured particles can be recovered quickly by re-entry into the flow stream.

Figures 5A, 5B:
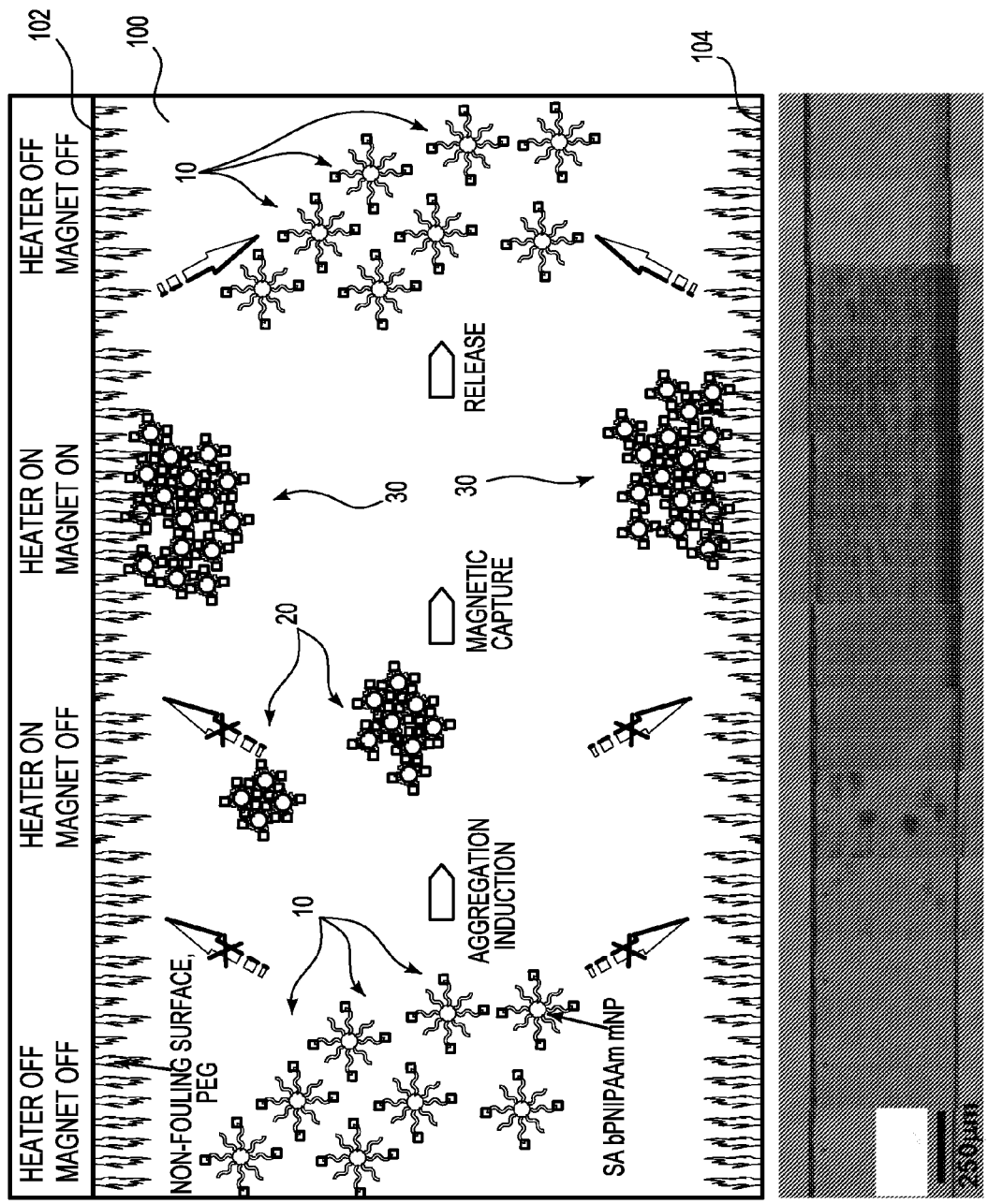
FIG. 5A is a schematic illustration of a representative device and method of the invention showing mNP capture and release.
FIG. 5B shows images of the corresponding micrographs. Capture and release of the PNIPAAm mNPs (steptavidin:biotin PNIPAAm mNPs, (SA bPNIPAAm mNP)) was demonstrated in PEGylated PDMS microfluidic channels having a channel width of 500 μm. The magnetic field was introduced by embedding a magnet on one side (lower) of the channel. The mNPs were flowed into the channel (reference numeral 100) having a non-fouling surface (reference numerals 102 and 104) with heater and magnetic field off (heater off, magnet off). A mNP solution (4 mg/mL) was injected into the channel with a constant flow (~1 μL/min). The mNPs are soluble and free flowing in the PEGylated channels when the temperature is below the LCST of the PNIPAAm mNPs (free flowing mNPs, reference numeral 10). As the mNPs flow into the heated region (heater on, magnet off), the temperature is above the LCST of the mNPs and the mNPs aggregate, but do not adhere to the non-fouling, PEGylated channel wall surfaces in the absence of an applied magnetic field (aggregated mNPs, reference numeral 20). The mNPs are captured onto the PEGylated channel walls only when the temperature is raised above the LCST, and the magnetic field is applied (heater on, magnet on) (captured aggregated mNPs, reference numeral 30). The reversal of the temperature and applied magnetic field (heater off, magnet off) results in the release and redispersion of the captured aggregated mNPs and their diffusive re-entry into the flow stream (free flowing mNPs, reference numeral 10).

A scheme for the representative PNIPAAm mNP separation system is shown in FIG. 5A. The mNPs are soluble and free flowing in the PEGylated channels (channel surfaces to which have been attached PEG-containing polymers) when the temperature was held below the LCST of the mNPs. The size of these PNIPAAm mNPs also gives them low magnetophoretic mobility, so that they are not captured by an applied magnetic field under flow conditions below the LCST. The mNPs can thus diffuse and capture targets as isolated particles below the LCST. As they flow into the heated region of a microchannel, the temperature is raised above the LCST of the PNIPAAm and the mNPs aggregate, but do not stick to the non-fouling, PEGylated channel walls in the absence of an applied magnetic field. The mNPs are captured onto the PEGylated channel walls only when the temperature is raised above the LCST, and the magnetic field is applied. The reversal of the temperature and applied magnetic field results in the redispersion of the aggregated mNPs and their diffusive re-entry into the flow stream.

The LCST was determined by cloud point measurements and found to be 32.4±0.1° C. for the PNIPAAm mNPs, 31.0±0.1° C. for bPNIPAAm mNPs, and 41.1±0.3° C. for SA-bPNIPAAm mNPs. The particle capture/release was demonstrated in PEGylated PDMS microfluidic channels with bPNIPAAm mNPs. The width of the channel was 500 μm. The magnetic field was introduced by embedding a magnet at the lower side of the channel. The mNP solution (4 mg/mL) was injected into the channels with a constant flow (~1 μL/min). After the injection of particle solution, the channel was maintained at the same temperature with the applied field and washed with buffer at the same flow rate.

Figure 6:
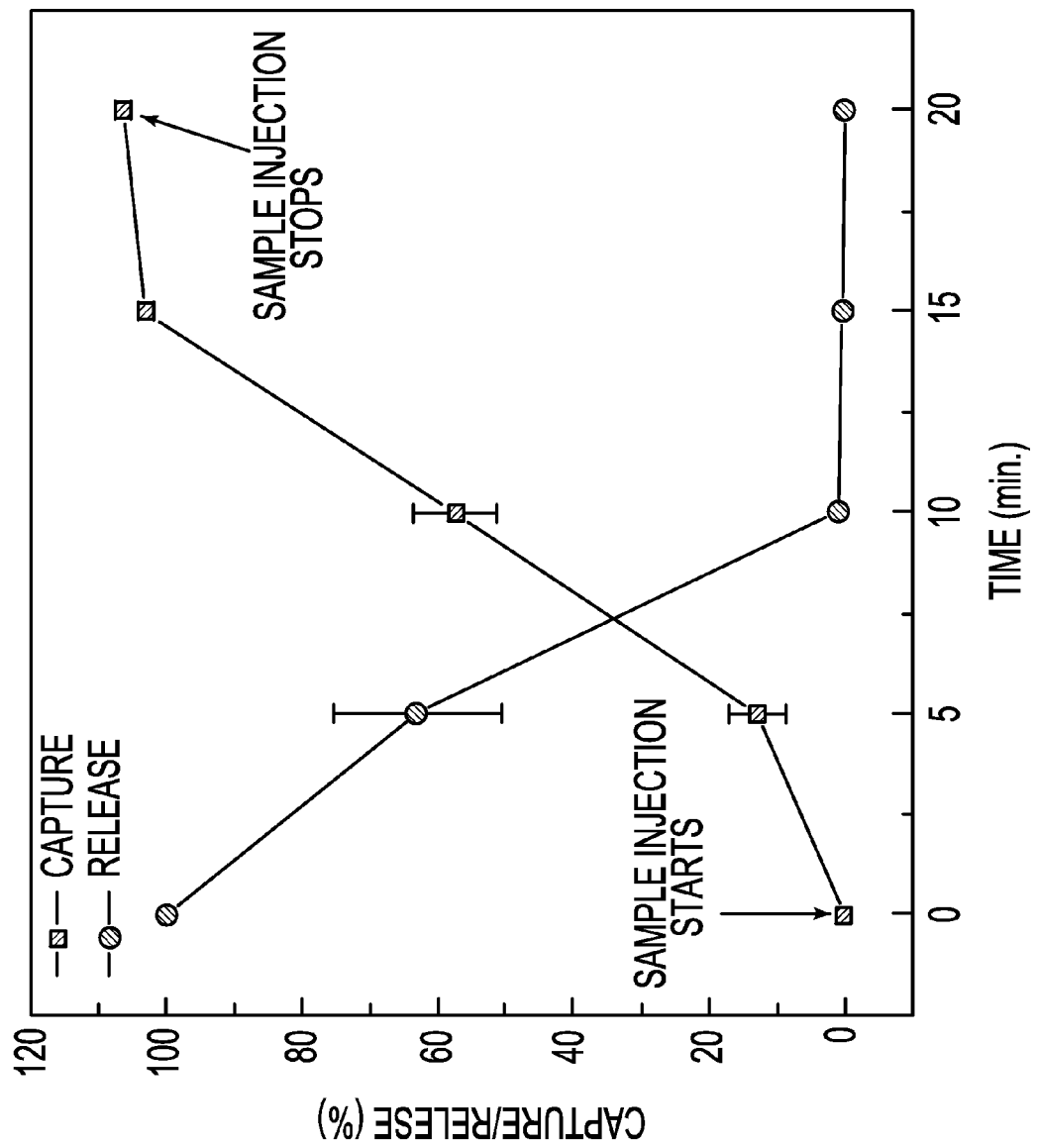
FIG. 6 is a graph illustrating the capture and release kinetics of representative mNPs of the invention (bPNIPAAm mNPs) in the PEGylated channel of FIG. 5. Starting from time zero (square curve), 20 μL of the mNPs were injected into the channel with a constant flow (~1 μL/min). The channel reached the maximum capture density within 15 minutes. When the temperature was reversed to below the LCST and the applied field was removed (time zero of release, circle curve), the captured particles were quantitatively released back into the flow stream within 10 minutes.

FIG. 5B shows the micrographs of the capture/release illustrated schematically in FIG. 5A. When the temperature was lower than the LCST, neither aggregation nor capture occurred. Once the temperature was raised above the LCST, the particles aggregated. When the temperature was higher than LCST and the applied field was on, the mNPs were captured because the aggregation results in an increase of $D_C$ and $\mu_m$. For the release study, buffer was injected (~1 μL/min) when the temperature was lower than the LCST and at zero applied field. The kinetic profile (FIG. 6) of the capture and release was determined by analyzing the capture micrographs. Starting from time zero, 20 μL of the mNPs were injected into the channel with a constant flow (~1 μL/min). The channel reached the maximum capture density within 15 minutes at this flow rate and mNP concentration. After the capture at the heated wall position, the channel was washed with 20 μL of buffer at the same flow rate. The captured mNPs are held stable during buffer washing. When the temperature was reversed to below the LCST and the applied field was removed (time zero of release), the captured particles were quantitatively released back into the flow stream within 10 minutes.

This representative system demonstrated the reversible magnetophoretic capture of the modified mNPs in PEGylated microfluidic channels as the $D_C$ and $\mu_m$ are increased in the aggregated state. By reversibly aggregating the particles at a controlled time point and channel position after the isolated mNP has reacted with target molecules, the advantages of a large surface/volume ratio and faster diffusion during target capture are retained, while optimizing $\mu_m$ for magnetic isolation after target capture.

Devices that utilize stimuli-responsive nanoparticles. In one aspect, the invention also provides devices for using the stimuli-responsive nanoparticle.

In one embodiment, the invention provides a device, comprising
(a) a channel adapted for receiving a flow comprising a plurality of stimulus-responsive magnetic nanoparticles, wherein the nanoparticle is reversibly self-associative in response to a stimulus; and
(b) a separation region through which the flow passes, wherein the separation region is adapted to reversibly apply a stimulus and a magnetic field to the flow to capture the nanoparticles.

In one embodiment, the device is a well of a multi-well plate. In one embodiment, the device is a microfluidic device having a channel. In one embodiment, the device's channel further comprises a surface having an array or plurality of capture regions. As used herein, the term "capture region" refers to a region of the surface of the channel coated with a plurality of stimulus-responsive polymers for capturing the nanoparticles. In one embodiment, the separation region is non-fouling. A representative device is illustrated in FIG. 5A.

The device useful in the invention permits reversible, stimuli-induced aggregation of the stimuli-responsive magnetic nanoparticles followed by magnetic field-induced aggregation of the stimuli-induced aggregates.

Assays that utilize stimuli-responsive nanoparticles. The invention also provides assays for using the stimuli-responsive nanoparticle.

In one embodiment, the invention provides an assay for detecting a diagnostic target, comprising:
(a) contacting the diagnostic target with a plurality of stimuli-responsive magnetic nanoparticles, wherein each nanoparticle comprises a capture moiety having affinity toward the diagnostic target;
(b) forming nanoparticle conjugates by combining the diagnostic target with the stimuli-responsive magnetic nanoparticles;
(c) aggregating the nanoparticle conjugates by applying an external stimulus;
(d) further aggregating the nanoparticle conjugates by subjecting the aggregated nanoparticle conjugates to a magnetic field;
(e) regenerating the nanoparticle conjugates by removing the stimulus and the magnetic field; and
(f) analyzing the regenerated nanoparticles comprising the diagnostic target.

In the above method, forming nanoparticle conjugates by combining the diagnostic target with the stimuli-responsive magnetic nanoparticles provides a conjugate that includes a diagnostic target bound to the capture moiety. In the above method, regenerating the nanoparticle conjugates by removing the stimulus and the magnetic field provides released, free flowing nanoparticle conjugates in which the diagnostic target is bound to the capture moiety.

The regenerated nanoparticles including the diagnostic target can be analyzed with or without release of the diagnostic target from the nanoparticle.

The diagnostic target can be a molecule that is indicative of a diseased condition or an indicator of exposure to a toxin, or a therapeutic drug that has been administered to a subject and whose concentration is to be monitored. The diagnostic target can be any protein, antibody, or nucleic acid related to a disease. In one embodiment, the diagnostic target is an antibody against hepatitis B virus. In one embodiment, the diagnostic target is an antibody against hepatitis C virus. In one embodiment, the diagnostic target molecule is an antibody against AIDS virus. In one embodiment, the diagnostic target molecule is the malaria parasitic antigen, or the antiplasmodial antibodies, or the parasitic metabolic products, or the plasmodia nucleic acid fragments. In one embodiment, the diagnostic target molecule is an antibody against tuberculosis bacteria. In one embodiment, the diagnosis target molecule is a dengue fever virus or antibody.

The following examples are provided for the purpose of illustrating, not limiting, the invention.

EXAMPLES

Example 1

The Preparation and Characterization of Representative Temperature-Responsive Nanoparticles In this example, the preparation and characterization of representative temperature-responsive nanoparticles of the invention is described.

Materials.
N-Isopropylacrylamide (NIPAAm) (Aldrich, 97%) was recrystallized from benzene/hexane 3:2 (v:v) and dried under vacuum prior to use. 2-dodecylsulfanylthiocarbonylsulfanyl-2-methyl propionic acid (DMP) is a gift from Noveon. Iron pentacarbonyl/Fe(CO)$_5$ (Aldrich, 99.999%), 4,4'-Azobis(4-cyanovaleric acid) (Aldrich, 75+%), tetraethylene glycol dimethyl ether/tetraglyme (Aldrich, 99%), N-hydroxysuccinimide/NHS (Aldrich, 98%), methanol (EMD, 99.8%), hexane (EMD, 89.2%), tetrahydrofuran/THF (EMD, 99.99+%), p-dioxane (EMD, 99%), biotin (Aldrich), HABA/avidin reagent (Aldrich), EZ-Link® Biotin-LC-PEO-Amine and N,N'-dicyclohexylcarbodiimide/DCC (Pierce) was used without any purification.

Synthesis of PNIPAAm.

Polymerization of PNIPAAm was performed according to a previously published protocol. Ebara, M., et al., *Lab on Chip* 6:843, 2006. The target molecular weight was 5,000. Briefly, 2 g of NIPAAm (monomer), 145 mg of DMP (trithiocarbonate-based chain transfer agent, CTA), and 6 mg of 4,4'-azobis (4-cyano-valeric acid) (initiator) were mixed with 5 mL of methanol. After purging with nitrogen for 20 min, this solution was sealed and maintained at 60'C overnight. The methanol was removed by purging air. The polymer was dissolved with THF and precipitated in pentane for purification. The sample was dried overnight in a vacuum oven.

Synthesis of PNIPAAm mNPs.

In a typical synthesis, 900 mg (0.18 mmol) of the polymer surfactant (M.W. ~5,000) was added to 50 mL of tetraglyme (preheated to 100° C.) and stirred for 5 min. Subsequently, 0.2 mL of $Fe(CO)_5$ (1.52 mmol) was injected into the solution and the temperature was raised to 190'C after 10 min stirring. The solution was refluxed for 5 hours, and then cooled down to room temperature. The product was precipitated in n-hexane and collected by centrifugation. The precipitate was redissolved in deionized water and dialyzed using a dialysis membrane of MW cut-off of 10,000 for 72 hrs. After the dialysis, the particles were collected by lyophilization.

Biotinylation of PNIPAAm mNPs (bPNIPAAm mNPs).

PNIPAAm mNPs were biotinylated via the carboxyl end group with carbodiimide chemistry. The end carboxyl groups were activated with DCC in the presence of NHS. The ratio of carboxyl group (PNIPAAm mNPs) to NHS to DCC was 1:1:1. PNIPAAm mNPs were dissolved in dioxane. The calculated amount of NHS/DCC solution, which was prepared by premixing NHS and DCC in dioxane, was slowly added (over 15 minutes) into the particle solution at 12° C. The mixed solution was stirred overnight and filtered to remove the urea. The desired amount of EZ-Link® biotin-LC-PEO-amine was predissolved in dioxane and added to the particle solution, which was then stirred overnight. The resulting solution was centrifuged to remove solids. The particles were precipitated with n-hexane followed by centrifugation and vacuum dried overnight. The particles were dialyzed against water with a dialysis membrane of MW cut-off of 10,000 for 72 hrs and collected by lyophilization.

Streptavidin-bPNIPAAm mNPs Conjugate (SA-bPNIPAAm mNPs).

To prevent crosslinking, an excess amount of SA was used. bPNIPAAm mNPs and lyophilized SAs were predissolved in 0.1 M PBS (pH=7.4, NaCl=0.15 M) separately. bPNIPAAm mNPs solution was added into the streptavidin solution slowly (over 30 min) at 4° C. The mixture was dialyzed against buffer using a dialysis membrane of MW cut-off of 100,000 for 72 hrs at 4° C.

Lower Critical Solution Temperature (LCST) Measurement.

The LCST was determined as the temperature at 50% of the maximum absorbance at 550 nm. The concentration of samples was 2 mg/mL in PBS. The data were collected using a UV-Vis spectrophotometer with a jacketed cuvette holder to control the temperature of the sample. A heating rate of 0.5° C./min was used, and absorbance values were measured every 0.5-1.0° C.

2-(4-Hydroxyphenylazo)benzoic Acid (HABA) Assay.

The biotinylation efficiency and SA loading were characterized with HABA assay, which used the HABA/avidin reagent from Sigma. A biotin solution (0.21 mg/mL) was used for the calibration. The concentration of the particles is 4 mg/mL in deionized water. The data were collected using a UV-Vis spectrophotometer. The cuvette with water was used as a blank. After the water was removed, 450 µL HABA/avidin reagent (reconstituted in deionized water) into were pipetted into the cuvette. The absorbance at 500 nm was recorded. 10 µL samples were added, mixed by inversion, and the absorbance recorded at 500 nm. Addition of the sample was repeated until the total volume of the sample was 50 µL. Because of the absorbance from the iron oxide core, PNIPAAm mNPs were used as the control.

Transmission Electron Microscopy (TEM).

Nanocrystal size and morphology were investigated using a Phillips EM-420T Transmission Electron Microscope (120 Kiev). Crystals suspended in water, deposited onto a carbon stabilized formvar-coated copper grid (400 mesh) and allowed to dry.

Powder X-Ray Diffraction (XRD).

Powder XRD was performed by using a Philips X-ray diffractometer 1820 (Cu $K_\alpha$ radiation, $\lambda=1.5418$ Å). Two-dimensional patterns were angle integrated to obtain the patterns displayed. The instrument resolution is 0.02° in 2θ, and the accumulation time for each sample was 41 minutes. The 2θ range used was from 20° to 70°. XRD samples were prepared by coating with several drops of nitrocellulose in amyl acetate (concentration 1%) on a quartz plate.

Magnetic Measurements.

Magnetic data of the solid samples were collected with a Quantum Design SQUID MPMS-XL (DC modes and maximum static field of ±5 T) in liquid helium and room temperatures. The temperature dependence of the magnetization was measured in the range 5-300 K in an applied field of 20 Oe, after cooling in zero magnetic field (ZFC) or by cooling in a field of 20 Oe (FC).

Example 2

The Preparation of a Stimuli-Responsive Microfluidic Separation System

SU-8 Master and PDMS Device Fabrication.

A silicon wafer was spin-coated with SU8-50 and baked at 95° C. for 1 h. The photoresist was exposed to UV light (Kaspar-Quintel model 2001 aligner) for 150 s through transparency masks. After exposure, the masters were baked at 95° C. for 10 min and developed with SU-8 developer (Microchem) for 15 min. The masters used in this study were 0.1 mm tall and 0.5 mm wide. Patterned masters and bare silicon wafers were passivated by 10 minute exposure to silane under vacuum. PDMS prepolymer was prepared by mixing PDMS base with a curing agent in a 10:1 ratio by weight and degassing the mixture under vacuum. To fabricate fluid channels, the mixture was cast against the pattered silicon master. To fabricate the lower surface, the mixture was cast over a bare silicon wafer. In both cases the samples were cured at 60° C. for 3 h. A piece of silicone tubing was embedded into the PDMS to create access inlets to the channels. PDMS devices were then assembled using $O_2$ plasma bonding.

ITO Heater Fabrication.

ITO heaters were patterned photolithographically by spin coating AZ 1512 onto ITO slides (Delta Technologies, Inc.) and exposing to UV through transparency photomasks. ITO etching was performed by immersing photoresist patterned slides for 7.5 minutes in $HNO_3$:$HCl$:$H_2O$ (1:4:15 by volume) warmed to 55° C. To fabricate electrical conductors, patterned ITO slides were then coated by 20 nm of chromium followed by 150 nm of gold by electron beam evaporation. Conductors were patterned photolithographically as described above. Gold and chromium were etched by 5 minutes exposure to TFA gold etchant followed by 5 minutes exposure to TFD chromium etchant. Copper wires were attached to the heater conductors using silver conductive epoxy.

UV-Induced Graft Polymerization.

UV-mediated grafting was directed according to a previously published protocol. Briefly, benzophenone, a photosensitizer was dissolved in acetone and flowed into the channel for less than one minute. The channel was then washed extensively with water. A solution containing PEG diacrylate (PEGDA), $NaIO_4$ (0.5 mM) as an oxygen scavenger, and benzyl alcohol (0.5 wt %) as a chain transfer agent was loaded into the channel, which was then irradiated with UV light (100 W, 365 nm, Ted Pella, Inc.).

While illustrative embodiments have been illustrated and described, it will be appreciated that various changes can be made therein without departing from the spirit and scope of the invention.

While illustrative embodiments have been illustrated and described, it will be appreciated that various changes can be made therein without departing from the spirit and scope of the invention.

The embodiments of the invention in which an exclusive property or privilege is claimed are defined as follows:

1. A stimuli-responsive magnetic nanoparticle responsive to a magnetic field, comprising:
    (a) a solid metal oxide core responsive to a magnetic field; and
    (b) a plurality of stimuli-responsive polymer molecules each having a proximal end comprising a micelle-forming moiety and a distal end comprising a stimuli-responsive moiety, wherein the micelle-forming moiety of each of the plurality of stimuli-responsive polymer molecules becomes incorporated within the solid metal oxide core by:
        (i) providing a first solution of the plurality of stimuli-responsive polymer molecules in a solvent that is a poor solvent for the micelle-forming moiety;
        (ii) forming a micelle in the first solution, wherein the micelle dimensions are spatially defined by the micelle-forming moieties;
        (iii) providing a second solution of a metal compound that is a precursor to the metal oxide core;
        (iv) introducing the second solution into the micelle, wherein the second solution is more soluble in the micelle than in the first solution, causing the second solution to preferentially concentrate in the micelle; and
        (v) solidifying the precursor within the micelle in order to incorporate the micelle-forming moiety of each of the plurality of stimuli-responsive polymer molecules within a solid metal oxide core;
    wherein the stimuli-responsive moiety is self-associative in response to a stimulus.

2. The nanoparticle of claim 1, wherein the metal oxide is selected from the group consisting of ferrous oxide, ferric oxide, gadolinium oxide, and mixtures thereof.

3. The nanoparticle of claim 1, wherein the stimuli-responsive polymer molecules respond to a stimulus selected from the group consisting of temperature, pH, light, electric field, and ionic strength.

4. The nanoparticle of claim 1, wherein the stimuli-responsive polymer molecules comprise a polymer having a balance of hydrophilic and hydrophobic groups.

5. The nanoparticle of claim 1, wherein the stimuli-responsive polymer molecules are temperature-responsive.

6. The nanoparticle of claim 1, wherein the stimuli-responsive polymer molecules comprise polymers or copolymers of N-isopropylacrylamide.

7. The nanoparticle of claim 1, wherein the stimuli-responsive polymer molecules are multi-responsive copolymer molecules.

8. The nanoparticle of claim 1, wherein the solid metal oxide core has a diameter of from about 2 nm to about 20 nm.

9. The nanoparticle of claim 1, wherein the micelle-forming moiety comprises a micelle-forming hydrophobic moiety.

10. The nanoparticle of claim 9, wherein the micelle-forming hydrophobic moiety comprises alkyl, polyester, polyamide, or polypeptide moieties.

11. The nanoparticle of claim 9, wherein the micelle-forming hydrophobic moiety comprises a n-dodecyl group.

12. The nanoparticle of claim 1, wherein the nanoparticle has a diameter from about 5 nm to about 30 nm.

13. A method of forming a stimuli-responsive magnetic nanoparticle responsive to a magnetic field, the method comprising:
    providing a first solution of a plurality of stimuli-responsive polymer molecules, each having a proximal end comprising a micelle-forming moiety and a distal end comprising a stimuli-responsive moiety, wherein the stimuli-responsive moiety is self-associative in response to a stimulus, and wherein the first solution comprises a solvent that is a poor solvent for the micelle-forming moiety;
    forming a micelle in the first solution, wherein the micelle dimensions are spatially defined by the micelle-forming moieties;
    providing a second solution of a metal compound that is a precursor to a solid metal oxide;
    introducing the second solution into the micelle, wherein the second solution is more soluble in the micelle than in the first solution, causing the second solution to preferentially concentrate in the micelle; and
    solidifying the precursor within the micelle in order to incorporate the micelle-forming moiety of each of the plurality of stimuli-responsive polymer molecules within a solid metal oxide core.

14. The method of claim 13, wherein the metal oxide is selected from the group consisting of ferrous oxide, ferric oxide, gadolinium oxide, and mixtures thereof.

15. The method of claim 13, wherein the stimuli-responsive polymer molecules respond to a stimulus selected from the group consisting of temperature, pH, light, electric field, and ionic strength.

16. The method of claim 13, wherein the stimuli-responsive polymer molecules comprise polymers or copolymers of N-isopropylacrylamide.

17. The method of claim 13, wherein the stimuli-responsive polymer molecules are multi-responsive copolymer molecules.

18. The method of claim 13, wherein the solid metal oxide core has a diameter of from about 2 nm to about 20 nm.

19. The method of claim 13, wherein the micelle-forming moiety comprises a micelle-forming hydrophobic moiety.

20. The method of claim 13, wherein the nanoparticle has a diameter from about 5 nm to about 30 nm.

* * * * *